(12) United States Patent
Imai et al.

(10) Patent No.: US 7,422,887 B2
(45) Date of Patent: Sep. 9, 2008

(54) PHOSPHOLIPASE A₂ AND GENE THEREOF

(75) Inventors: Yuji Imai, Hyogo (JP); Koji Wakimoto, Saitama (JP); Hiroaki Chiba, Nara (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 274 days.

(21) Appl. No.: 10/501,675

(22) PCT Filed: Jan. 17, 2003

(86) PCT No.: PCT/JP03/00328

§ 371 (c)(1), (2), (4) Date: Jul. 16, 2004

(87) PCT Pub. No.: WO03/060132

PCT Pub. Date: Jul. 24, 2003

(65) Prior Publication Data

US 2005/0282161 A1 Dec. 22, 2005

(30) Foreign Application Priority Data

Jan. 17, 2002 (JP) ............................. 2002-008435

(51) Int. Cl.
*C12N 9/18* (2006.01)
*C12Q 1/34* (2006.01)
*C12Q 1/68* (2006.01)
*C07H 21/04* (2006.01)

(52) U.S. Cl. .......................... 435/197; 435/18; 435/6; 536/23.2; 536/23.5; 536/24.3; 536/24.31

(58) Field of Classification Search ................ 435/197, 435/18, 6; 536/23.2, 23.5, 24.3, 24.31
See application file for complete search history.

(56) References Cited

U.S. PATENT DOCUMENTS 6,025,178 A 2/2000 Choin et al.
6,287,838 B1 9/2001 Kriz et al.

FOREIGN PATENT DOCUMENTS

WO WO 02/04490 A2 1/2002
WO WO 02/31162 A2 4/2002

OTHER PUBLICATIONS

Sequence alignment of SEQ ID No. 8 with Accession No. AD36478; Apr. 18, 2002.*
Sequence aligmnment of SEQ ID No. 9 with Accession No. AAE22843; Apr. 18, 2002.*
Sequence alignment of SEQ ID No. 8 with Accession No. ABA94700; Jan. 17, 2002.*
Sequence alignment of SEQ ID No. 9 with SEQ ID No. 6 of US 20040029136A1, Feb. 12, 2004.*
Chiba H. et al., "Cloning of a Gene for a Novel Epithelium-specific Cytosolic Phospholipase A₂, cPLA₂δ, Induced in Psoriatic Skin", (Mar. 26, 2004), The Journal of Biological Chemistry, vol. 279, No. 13, pp. 12890-12897.
Clark J. D. et al., "A Novel Arachidonic Acid-Selective Cytosolic PLA₂ Contains a Ca²⁺-Dependent Translocation Domain with Homology to PKC and GAP", (Jun. 14, 1991), Cell, vol. 65, pp. 1043-1051.
Clark J.D. et al., GenBank Ac. No. M72393, sequence list, May 23, 1996.
Pickard R.T. et al., "Molecular Cloning of Two New Human Paralogs of 85-kDa Cytosolic Phospholipase A₂", (Mar. 26, 1999), The Journal of Biological Chemistry, vol. 274, No. 13, pp. 8823-8831.
Pickard R.T., GenBank Ac. No. AF065215, sequence list, Mar. 23, 1999.
Song C. et al., "Molecular Characterization of Cytosolic Phospholipase A₂-β", (Jun. 11, 1999), The Journal of Biological Chemistry, vol. 274, No. 24, pp. 17063-17067.
Underwood K.W. et al., "A Novel Calcium-independent Phospholipase A₂, cPLA₂-γ, That Is Prenylated and Contains Homology to cPLA₂", (Aug. 21, 1998), The Journal of Biological Chemistry, vol. 273, No. 34, pp. 21926-21932.
Underwood K.W. et al., GenBank AF058921, sequence list, Aug. 26, 1998.

* cited by examiner

*Primary Examiner*—Tekchand Saidha
*Assistant Examiner*—Malgorzata A Walicka
(74) *Attorney, Agent, or Firm*—Browdy and Neimark, PLLC

(57) ABSTRACT

To provide a novel phospholipase A₂ (PLA₂) associated with psoriasis, a nucleic acid encoding the same, a method for characterizing, identifying or screening an inhibitor for the PLA₂ or a medicament; and a novel method for diagnosis or examination of psoriasis or the like. A polypeptide having the amino acid sequence shown in SEQ ID NO: 9, a conservative substitution variant thereof, a naturally occurring allelic variant thereof, or the like. A nucleic acid encoding the above-mentioned polypeptide, a complement thereof or the like. A method for characterizing, identifying or screening an inhibitor for the PLA₂ or a medicament, using the above-mentioned polypeptide. An examination method for psoriasis, characterized by assaying an expression level of a gene consisting of the above-mentioned nucleic acid or the like.

6 Claims, 3 Drawing Sheets

PHOSPHOLIPASE A$_2$ AND GENE THEREOF

TECHNICAL FIELD

The present invention relates to a novel phospholipase A$_2$ associated with psoriasis, a nucleic acid encoding the same and a method of using the same; a method for producing the phospholipase A$_2$, and a recombinant vector or a host cell usable therefor; an antibody capable of recognizing the phospholipase A$_2$; a method for characterizing, identifying or screening an inhibitor of the phospholipase A$_2$ or a medicament; a method for inhibiting the phospholipase A$_2$; a pharmaceutical composition for treating an inflammatory dermal disease and a process for preparing the same; a method for treating an inflammatory dermal disease; and an examination method for psoriasis.

BACKGROUND ART

Psoriasis is one of inflammatory keratosis syndromes, and is a chronic intractable dermal disease characterized by scale. Psoriasis is a disease repeating remission and animus in many cases, and there is no decisive method for treating psoriasis to date.

Psoriasis is roughly classified into five types (1) psoriasis vulgaris, (2) erythroderma psoriaticum, (3) psoriasis arthropica, (4) psoriasis guttata, and (5) pustular psoriasis, based on the pathologic characteristics. Among them, psoriasis vulgaris, of which patients are largest in number, is a disease accounting for about 80% of all the patients with psoriasis, and pustular psoriasis is a disease accompanied with systemic symptom, leading to death in some cases. In any type, pathology of psoriasis is accompanied with both of immunological abnormality in epidermis and dermis, and abnormality in proliferation and differentiation of an epidermic keratinocyte.

Causes of onset for psoriasis are involved in both of genetic background and exogenous factor, and the psoriasis is developed by exposing any exogenous or endogenous factor to a person having a certain kind of genetic background.

It is well known that the genetic factor is related to the onset of psoriasis. In Europe and the U.S.A., a ratio of familial development thereof is about one-third, and an incidence rate of psoriasis in monozygotic twin shows 72%, which is high consistency to the others, and incidence rate of psoriasis in dizygotic twin is as low as 22%. As described above, in psoriasis, although it is certain that a genetic factor is an important cause of onset, but its hereditary manner is not clear. In addition, it is considered that there are little cases of onset caused by a single gene, so that onset is caused by multiple genes in many cases.

PSOR1 (Psoriasis susceptibility) gene localized in HLA antigen gene region of chromosome 6 is a psoriasis-sensitive gene which was happened to be found by typing of the HLA during the kidney transplantation. As genes involved in the onset of psoriasis, in addition to this PSOR1 gene, several kinds of genes localized in chromosome 1, chromosome 3, chromosome 4, chromosome 16, chromosome 17, chromosome 19, and chromosome 20, have been reported to date.

However, there are many points in the mechanisms of onset of psoriasis which have not yet been clarified, and the development of a therapeutic method or the like is difficult. In order to connect to the development of a new diagnostic or therapeutic method, advancements in research and analysis of a gene involved in the onset of psoriasis (psoriasis-associated gene) has been desired.

Pathologies of psoriasis and the like are summarized in some reviews (Bos et al., *Immunol. Today,* 20, 40-46, 1999 ; Baker et al., *Clin. Exp. Dermatol.,* 26, 321-325, 2001).

On the other hand, the phospholipase A$_2$ has been known as an enzyme involved in inflammatory diseases. The phospholipase A$_2$ is an enzyme which catalyzes a reaction in which an ester bond at 2-position of a glycerophospholipid is hydrolyzed to generate equimolar amounts of a free fatty acid and a lysophospholipid. Arachidonic acid released from glycerophospholipid constituting a biomembrane by action of phospholipase A$_2$ is converted into leukotrienes by lipoxygenase or the like, or converted into prostaglandins with cyclooxygenase or the like, or further converted into thromboxane A$_2$ or the like by action of thromboxane synthase on the prostaglandins. Since it has been revealed that these eicosanoids (leukotrienes, prostaglandins, and thromboxanes) are closely involved with various inflammations, allergic reactions, and ischemic diseases, the phospholipase A$_2$ plays a key role as an enzyme which raises a primary reaction that results in production of inflammatory mediators downstream of arachidonic acid.

It has been known that the phospholipase A$_2$ has at least 17 kinds of molecular species. These molecular species are classified into four subclasses (secretary phospholipase A$_2$, cytoplasmic phospholipase A$_2$, Ca$^{2+}$-independent phospholipase A$_2$, and platelet activating factor acetylhydrolase), based on similarities in structure and characteristics.

Among them, as cytoplasmic phospholipase A$_2$ (cPLA$_2$), which is high-molecular weight phospholipase A$_2$ localized in a cytoplasm, three molecular species [cPLA$_2\alpha$ (GenBank Ac. No. M72393; Clark et al., *Cell,* 65, 1043-1051, 1991), cPLA$_2\beta$ (GenBank Ac. No. AF065215; Pickard et al., *The Journal of Biological Chemistry,* 274, 8823-8831, 1999), cPLA$_2\gamma$ (GenBank Ac. No. AF058921; Underwood et al., *The Journal of Biological Chemistry,* 273, 21926-21932, 1998)] have been so far identified. cPLA$_2\gamma$ exhibits activity in a Ca$^{2+}$ concentration-independent manner. On the other hand, cPLA$_2\alpha$ and cPLA$_2\beta$ each has a phospholipid-binding region at N-terminal side of a protein molecule, and exhibits its activity by binding to a phospholipid membrane in a Ca$^{2+}$ concentration-dependent manner. However, since the amount of Ca$^{2+}$ required for exhibiting the activity is on the order of μM, it is considered that these also exhibit their activities in cytoplasm.

The phospholipase A$_2$ is an important target molecule in the development and research of therapeutic drugs for inflammatory diseases, and studies of inhibitors thereof have been advanced intensively. There are some cases where inhibitory action for the phospholipase A$_2$ has been found in known medicaments. In addition, it has been also found that a specific phospholipase A$_2$ inhibitor can serve as a useful therapeutic drug.

In order to develop an excellent medicament having high therapeutic effects and little side effects, it has been desired to screen an inhibitor having a high selectivity on a particular type of the phospholipase A$_2$ to be targeted.

Further, it has been also desired to find a novel type of the phospholipase A$_2$, which is a different molecular species from those of conventional ones, for the studies of the mechanism of onset of inflammatory diseases, and for the possibility to be used as a target molecule of a novel therapeutic drug.

DISCLOSURE OF INVENTION

An object of the present invention is to provide a novel type of a phospholipase A$_2$ and a nucleic acid encoding the same, associated with psoriasis. In addition, there are provided a novel method for characterizing, identifying or screening a phospholipase $A_2$ inhibitor or a medicament, and a new method for diagnosis and examination for psoriasis. Also, objects of the present invention other than the objects as described above will be apparent from the following description.

Regarding the psoriasis, conventionally, even comprehensive genetic analysis has not been performed. Using the body map method developed by Okubo et al. (*Methods in Molecular Genetics*, 5, 17-33, 1994), the present inventors have found a psoriasis-associated gene (GS21015 gene), of which expression is specifically increased in epidermis of a patient with psoriasis, by intensively comparing and studying genes expressed in epidermis of a patient with psoriasis with those of a normal individual. Further, the present inventors have found that a polypeptide encoded by the gene is a novel phospholipase $A_2$, and succeeded in expression of the phospholipase $A_2$ in a cell by genetic recombination technique. The present invention has been completed thereby.

Concretely, the present invention relates to:

[1] a polypeptide selected from the following (a) or (b):
(a) a polypeptide having the amino acid sequence shown in SEQ ID NO: 9; or
(b) a polypeptide selected from the group consisting of the following (i) to (iv):
  (i) a polypeptide which is a conservative substitution variant or a naturally occurring allelic variant of the polypeptide having the amino acid sequence shown in SEQ ID NO: 9;
  (ii) a polypeptide having an amino acid sequence having a sequence homology of 75% or more, as compared to a full length amino acid sequence shown in SEQ ID NO: 9;
  (iii) a polypeptide having an amino acid sequence in which one or more amino acids in the amino acid sequence shown in SEQ ID NO: 9 are deleted, substituted or added; and
  (iv) a polypeptide encoded by a nucleic acid capable of hybridizing with a nucleic acid having the nucleotide sequence shown in SEQ ID NO: 8 under stringent conditions, or by a complement thereof,
  wherein the polypeptide possesses a phospholipase $A_2$ activity;

[2] the polypeptide according to the above [1], wherein the polypeptide is a polypeptide of human;

[3] the polypeptide according to the above [1], wherein the polypeptide is a recombinant polypeptide;

[4] a nucleic acid encoding the polypeptide of the above [1];

[5] the nucleic acid according to the above [4], wherein the encoded polypeptide is a polypeptide of human;

[6] a nucleic acid selected from the following (a) or (b):
(a) a nucleic acid having the nucleotide sequence shown in SEQ ID NO: 8; or
(b) a nucleic acid selected from the following (I) or (II):
  (I) a nucleic acid capable of hybridizing with a nucleic acid having the nucleotide sequence shown in SEQ ID NO: 8 under stringent conditions, or a complement thereof; or
  (II) a nucleic acid having a nucleotide sequence having a sequence homology of 70% or more, as compared to a full length translation region sequence in the nucleotide sequence shown in SEQ ID NO: 8,
  wherein the nucleic acid encodes a polypeptide possessing a phospholipase $A_2$ activity;

[7] the nucleic acid according to the above [6], wherein the nucleic acid is a nucleic acid of human;

[8] a nucleic acid selected from the following (I) or (II):
  (I) a nucleic acid capable of hybridizing with a nucleic acid having the nucleotide sequence shown in SEQ ID NO: 8 under stringent conditions, or a complement thereof; or
  (II) a nucleic acid having a nucleotide sequence having a sequence homology of 70% or more, as compared to a full length translation region sequence in the nucleotide sequence shown in SEQ ID NO: 8,
wherein the nucleic acid is usable for the following (A) or (B):
(A) detection of expression or presence of a gene comprising the nucleic acid of any one of the above [4] to [7]; or
(B) change of expression of a gene comprising the nucleic acid of any one of above [4] to [7];

[9] the nucleic acid according to any one of the above [4] to [8], wherein the nucleic acid is an isolated nucleic acid;

[10] a recombinant vector comprising the nucleic acid of any one of the above [4] to [8];

[11] the recombinant vector according to the above [10], wherein the recombinant vector is an expression vector;

[12] a host cell into which the recombinant vector of the above [11] is introduced;

[13] a method for producing a recombinant polypeptide, comprising the steps of:
1) culturing a host cell into which the recombinant vector of the above [11] is introduced, to give a culture; and
2) collecting a polypeptide of a phospholipase $A_2$ encoded on the recombinant vector from the culture obtained in the above step 1);

[14] an antibody capable of recognizing the polypeptide of any one of the above [1] to [3];

[15] a method for characterizing, identifying or screening a therapeutic agent for an inflammatory dermal disease, comprising contacting a phospholipase $A_2$ comprising the polypeptide of any one of the above [1] to [3] with a test substance; and assaying an action of the test substance on the phospholipase $A_2$, to determine inhibition of the phospholipase $A_2$;

[16] the method according to the above [15], wherein the action of the test substance is assayed by carrying out an enzymatic reaction in a reaction system comprising the phospholipase $A_2$, a substrate for the phospholipase $A_2$ and the test substance, and assaying an inhibitory action for the enzymatic activity of the phospholipase $A_2$;

[17] the method according to the above [16], wherein the substrate is a glycerophospholipid, and the enzymatic activity is an activity for hydrolyzing an ester bond at 2-position of the glycerophospholipid;

[18] a method for inhibiting a phospholipase $A_2$ in human, comprising administering a test substance to a human individual who is a patient with an inflammatory dermal disease, wherein the test substance is determined to be a substance capable of inhibiting the phospholipase $A_2$, by assaying an action of the test substance on the phospholipase $A_2$ comprising the polypeptide of any one of the above [1] to [3];

[19] a method of selling a test substance or a composition containing the test substance as a therapeutic agent for an inflammatory dermal disease, wherein the test substance is determined to be a substance capable of inhibiting a phospholipase $A_2$, by assaying an action of the test substance on the phospholipase $A_2$ comprising the polypeptide of any one of the above [1] to [3];

[20] a method for manufacturing a pharmaceutical composition for the treatment of an inflammatory dermal disease, comprising mixing a test substance with a carrier, wherein the test substance is determined to be a substance capable of inhibiting the phospholipase $A_2$ by assaying an action of the test substance on the phospholipase A$_2$ comprising the polypeptide of any one of the above [1] to [3];

[21] a method of use of a phospholipase A$_2$ comprising the polypeptide of any one of the above [1] to [3], for the manufacture of a therapeutic agent for an inflammatory dermal disease;

[22] the method according to any one of the above [15] to [21], wherein the inflammatory dermal disease is a chronic intractable dermal disease;

[23] the method according to any one of the above [15] to [21], wherein the inflammatory dermal disease is psoriasis;

[24] the method according to any one of the above [15] to [21], wherein the test substance is a compound which has not been known as an inhibitor for the phospholipase A$_2$;

[25] a pharmaceutical composition for the treatment of an inflammatory dermal disease, comprising a compound capable of inhibiting a phospholipase A$_2$ comprising the polypeptide of any one of the above [1] to [3] as an active ingredient;

[26] a method for treating an inflammatory dermal disease, comprising administering to a patient an effective amount of a compound capable of inhibiting a phospholipase A$_2$ comprising the polypeptide of any one of the above [1] to [3];

[27] an examination method for psoriasis, characterized by assaying an expression level of a gene encoding the polypeptide of any one of the above [1] to [3] for a biological sample collected from a human or non-human animal individual;

[28] the examination method according to the above [27], wherein the expression level is assayed using a nucleic acid capable of hybridizing with a nucleic acid having the nucleotide sequence shown in SEQ ID NO: 8 under stringent conditions, or a complement thereof as a probe or primer;

[29] the examination method according to the above [28], wherein the probe or primer is a nucleic acid having the nucleotide sequence shown in SEQ ID NO: 4 or a complement thereof; and

[30] the examination method according to the above [27], wherein the expression level is assayed using an antibody capable of recognizing the polypeptide of any one of the above [1] to [3].

BEST MODE FOR CARRYING OUT THE INVENTION

Figure 1:
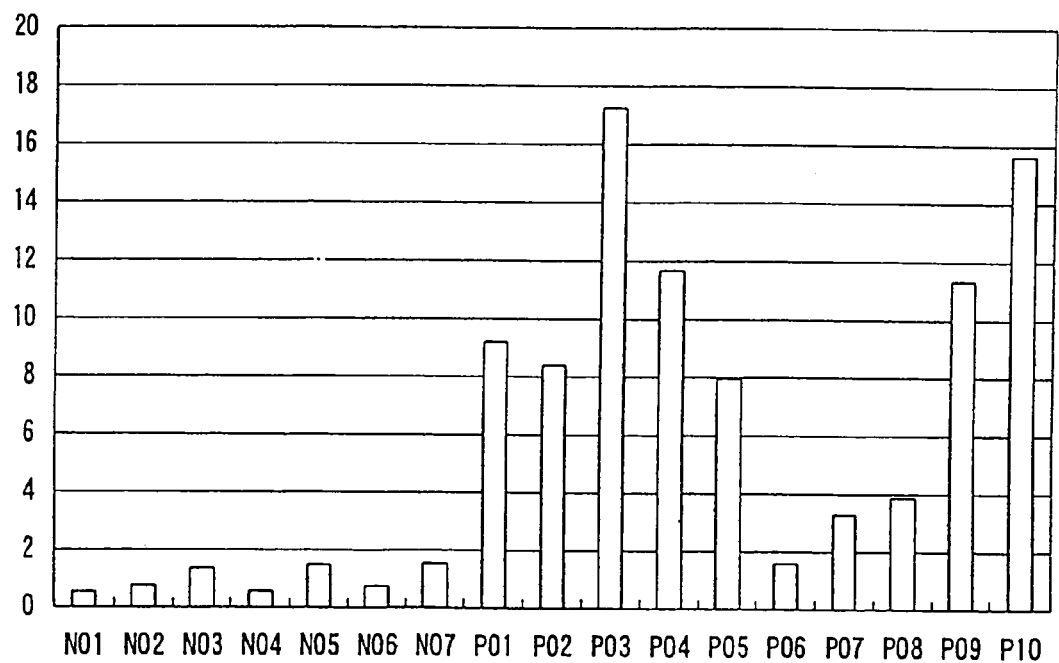
FIG. 1 is a diagram showing results of analysis of an expression level of a GS21015 gene in skin tissue samples from a normal individual and a patient with psoriasis by iAFLP method. In the figure, "N01", "N02", "N03", . . . and "N07" indicate a tissue sample of a normal individual, and "P01", "P02", "P03", . . . and "P10" indicate a tissue sample of a patient with psoriasis.

In the present specification, SEQ ID NO: 8 in the Sequence Listing set forth below shows a nucleotide sequence of a human cDNA containing a full length translational region of a psoriasis-associated gene (GS21015 gene) found by the inventors, and SEQ ID NO: 9 shows an amino acid sequence of a human polypeptide (GS21015) encoded by the above-mentioned cDNA.

The phospholipase A$_2$ comprising the polypeptide of the present invention and the nucleic acid encoding the same are useful as a novel target molecule in research and development of a therapeutic agent for a disease (especially a therapeutic agent for an inflammatory disease). Inter alia, the above-mentioned phospholipase A$_2$ and the nucleic acid are specifically expressed in a skin tissue, and expression thereof is increased in a psoriatic tissue as compared to a normal tissue. Therefore, the phospholipase A$_2$ and the nucleic acid are useful in research and development of a therapeutic agent for an inflammatory dermal disease such as psoriasis. In addition, the phospholipase A$_2$ and the nucleic acid are also useful in studies of onset mechanism of an inflammatory disease.

In the present invention, the polypeptide includes a recombinant polypeptide or an isolated polypeptide. In addition, in the present invention, the nucleic acid includes DNA molecules and RNA molecules, including a recombinant nucleic acid or an isolated nucleic acid. In addition, these nucleic acids include a single-stranded nucleic acid and a double-stranded nucleic acid. For instance, the nucleic acid having the nucleotide sequence shown in SEQ ID NO: 8 includes a single-stranded DNA having the nucleotide sequence, a double-stranded DNA consisting of a single-stranded DNA having the nucleotide sequence and a complement thereof, an RNA molecule corresponding thereto, and the like. The "complement" as used herein as a constituent of the above-mentioned double-stranded DNA refers to a complete complement to the above-mentioned single-stranded DNA.

The polypeptide of the present invention includes, for instance, but is not limited to, a polypeptide having the amino acid sequence shown in SEQ ID NO: 9. The present invention encompasses naturally occurring variants, artificially modified variants, homologs and orthologs from a heterogeneous organism and the like, of the polypeptide having the amino acid sequence shown in SEQ ID NO: 9.

In other words, besides the polypeptide having the amino acid sequence shown in SEQ ID NO: 9, the polypeptide of the present invention includes variants such as conservative substitution variants and naturally occurring allelic variants thereof.

The polypeptides (the above-mentioned variants) as described above may be any ones as long as they have the same biological activity [i.e. phospholipase A$_2$ activity (more specifically activity of hydrolyzing an ester bond of a glycerophospholipid at 2-position)] as that of the polypeptide having the amino acid sequence shown in SEQ ID NO: 9. The amino acid sequence of the polypeptide (the above-mentioned variant) described above has, for instance, a sequence homology of usually about 75% or more, preferably about 80% or more, more preferably about 85% or more, further preferably about 90% or more, still further preferably about 95% or more, as compared to the full length amino acid sequence shown in SEQ ID NO: 9. Alternatively, the polypeptide as described above (the above-mentioned variant) includes a polypeptide encoded by a nucleic acid capable of hybridizing with a nucleic acid having the nucleotide sequence shown in SEQ ID NO: 8 under stringent conditions, or a complement thereof.

In the "sequence identity" regarding an amino acid sequence as used herein, a value calculated using FASTA algorithm or BLAST algorithm is applied. In BLAST algorithm, conditions are open gap penalty 5, extend gap penalty 2, and word length 11.

In addition, the polypeptide of the present invention includes a polypeptide having one or more conservative amino acid substitutions as compared to the polypeptide having the amino acid sequence shown in SEQ ID NO: 9.

The polypeptide as described above has an amino acid sequence in which one or more amino acids are deleted, substituted or added in the amino acid sequence shown in SEQ ID NO: 9. Deletion, substitution, or addition of the amino acids may be to an extent that the biological activities [i.e. phospholipase $A_2$ activity (more specifically activity of hydrolyzing an ester bond of a glycerophospholipid at 2-position)] are not lost, and is usually 1 to about 200 in number, preferably 1 to about 160 in number, more preferably 1 to about 120 in number, further preferably 1 to about 80 in number, still further preferably 1 to about 40 in number.

The above-mentioned "conservative substitution variant" refers to a variant having the substitution of amino acid residues that are capable of maintaining physiological activities possessed by the polypeptide, and equivalent physicochemical properties regarding characteristic shape in a configuration, hydrophobicity, electric charge, pK and the like, in a living body. The "conservative substitution" includes a substitution between an amino acid residue in the amino acid sequence shown in SEQ ID NO: 9 and other amino acid belonging to the same group in any group of the following Group 1 to Group 6:

Group 1: glycine, alanine;
Group 2: valine, isoleucine, leucine;
Group 3: aspartic acid, glutamic acid, asparagine, glutamine;
Group 4: serine, threonine;
Group 5: lysine, arginine; and
Group 6: phenylalanine, tyrosine.

In order not to lose the phospholipase $A_2$ activity, it is desirable that an amino acid sequence is more highly conserved in a region controlling the activity, i.e., a catalytic region, than in other regions.

The catalytic region includes, for instance, regions corresponding to 275th to 525th amino acid residues (catalytic region A) and 613th to 798th amino acid residues (catalytic region B) in the amino acid sequence shown in SEQ ID NO: 9. Deletion, substitution or addition of the amino acids in each of the catalytic regions is usually 1 to about 20, preferably 1 to about 10, more preferably 1 to about 5, respectively. The amino acid sequence of each of the catalytic regions of the polypeptide described above has a sequence homology of usually about 90% or more, preferably about 95% or more, more preferably about 97% or more, respectively, as compared to each of the catalytic regions existing in the amino acid sequence shown in SEQ ID NO: 9. On the other hand, the deletion, substitution or addition of the amino acids in the non-catalytic region is usually 1 to about 160, preferably 1 to about 140, more preferably 1 to about 110, further preferably 1 to about 80, still further preferably 1 to about 40.

The nucleic acid (DNA or RNA) of the present invention includes, for instance, but is not limited to, a nucleic acid having the nucleotide sequence shown in SEQ ID NO: 8. The present invention encompasses naturally occurring variants, artificially modified variants, homologs and orthologs from a heterogeneous organism and the like, of the nucleic acid having the nucleotide sequence shown in SEQ ID NO: 8.

Specifically, besides the nucleic acid having the nucleotide sequence shown in SEQ ID NO: 8, the nucleic acid of the present invention includes a nucleic acid capable of hybridizing with a nucleic acid having the nucleotide sequence shown in SEQ ID NO: 8 under stringent conditions (more preferably, under high-stringent conditions), or a complement thereof (nucleic acid having complementary sequences).

The nucleotide sequence of the nucleic acid as described above has a sequence homology of usually 70% or more, preferably about 80% or more, more preferably about 85% or more, further preferably 90% or more, still further preferably 95% or more, as compared to a full length translational region sequence in the nucleotide sequence shown in SEQ ID NO: 8.

In addition, it is preferable that the nucleic acid as described above encodes a polypeptide having a phospholipase $A_2$ activity (more specifically activity of hydrolyzing an ester bond of a glycerophospholipid at 2-position).

In the present invention, the hybridization under stringent conditions can be usually carried out by hybridizing under a temperature condition of 50° to 65° C. for about 16 hours in 6×SSC (composition of 1×SSC: 0.15 M NaCl, 0.015 M sodium citrate, pH 7.0) or in a hybridization solution having a salt concentration equivalent thereto, pre-washing in 6×SSC or in a solution having a salt concentration equivalent thereto if needed, and thereafter washing in 1×SSC or in a solution having a salt concentration equivalent thereto. In addition, under the conditions of even higher stringency (under high-stringent conditions), the hybridization can be carried out by washing in 0.1×SSC or in a solution having a salt concentration equivalent thereto in the above-mentioned hybridization. Concretely, for instance, there can be carried out by hybridizing at 65° C. for 16 hours in a hybridization solution (6×SSC, 0.5% SDS, 5× Denhardt's solution, 100 μg/ml salmon sperm DNA), washing at 65° C. for 5 minutes in a washing solution (2×SSC, 0.5% SDS), and thereafter washing twice at 65° C. for 30 minutes in a washing solution (0.1×SSC, 0.5% SDS).

The sequence identity regarding the nucleotide sequence as used herein is a value calculated using FASTA algorithm or BLAST algorithm. In BLAST algorithm, conditions are open gap penalty 5, extend gap penalty 2 and word length 11.

The polypeptide and the nucleic acid of the present invention can be isolated and obtained using a tissue and a cell of a mammal as a source. The mammal includes a non-human animal such as dog, cattle, horse, goat, sheep, monkey, pig, rabbit, rat and mouse, as well as human. Among them, for the utilization in research and development of therapeutic agents for human, it is desirable to use those derived from human.

The nucleic acid of the present invention can be obtained by utilizing the sequence information (SEQ ID NO: 8 in the Sequence Listing set forth below) disclosed herein. For instance, primers and probes are designed on the basis of the information of the disclosed nucleotide sequences, so that the nucleic acid can be selected and obtained from a DNA library by appropriately combining PCR (polymerase chain reaction) method, colony hybridization method and plaque hybridization method using these primers and probes.

For instance, a cDNA is synthesized from mRNA prepared from a cell or a tissue of a mammal, and a cDNA fragment corresponding to a nucleic acid of the present invention or a part thereof is obtained by PCR method using the resulting cDNA as a template. A cDNA library is screened by colony hybridization method or plaque hybridization method using the resulting cDNA fragment as a probe, whereby a full length cDNA can be obtained. Also, a genomic gene can be isolated by screening a genomic DNA library. In addition, the homolog or the ortholog derived from a heterogeneous organism can be isolated by screening a DNA library of other mammal. The PCR method and the hybridization method in the screening can be carried out by referring to temperature conditions and the like described herein.

The DNA library such as a cDNA library and a genomic DNA library can be prepared in accordance with the method described in "Molecular Cloning 2nd Edition" (authored by Sambrook, J., Fritsch, E. F. and Maniatis, T., published on 1989 by Cold Spring Harbor Laboratory Press). Alternatively, when there is a commercially available library, this library may be used.

By sequencing the resulting cDNA, a translational region encoding a polypeptide which is the gene product can be determined, so that an amino acid sequence of this polypeptide can be obtained.

The polypeptide of the present invention can be obtained by isolation or purification from an extract of a tissue or a cell of a mammal. Alternatively, the polypeptide of the present invention can be produced by overexpression as a recombinant polypeptide by a conventional gene recombination technique. Alternatively, there can be expressed and produced in the form of a fusion polypeptide with other polypeptide (fusion partner). The above-mentioned fusion partner includes, for instance, but is not limited to, histidine tag, glutathione-S-transferase and the like.

The recombinant polypeptide can be produced, for instance, by culturing a host cell into which a recombinant expression vector comprising the nucleic acid of the present invention is introduced, and collecting the desired recombinant polypeptide from the cell culture (supernatant of culture, cell extract of cultured cell, and the like). The present invention encompasses a host cell into which a recombinant expression vector comprising the nucleic acid of the present invention is introduced (hereinafter also referred to as transformed cell), and a method for producing a recombinant polypeptide using the host cell.

The method for producing a recombinant polypeptide of the present invention is a method comprising the steps of:
1) culturing a host cell into which a recombinant vector comprising the nucleic acid of the present invention is introduced, to obtain a culture; and
2) collecting a polypeptide of a phospholipase $A_2$ encoded by the recombinant vector from the culture obtained in the above-mentioned step 1).

The recombinant expression vector and the transformed cell for overexpression of the recombinant polypeptide can be obtained, for instance, as follows. First, a nucleic acid encoding the polypeptide of the present invention is inserted into a vector in the form that is ligated at downstream of an appropriate promoter, to construct an expression vector. Next, the resulting expression vector is introduced into a host cell.

The expression system (host-vector system) includes, for instance, expression systems of bacterium, yeast, insect cell and mammal cell, and the like. Among them, in order to obtain a polypeptide having a well conserved function, it is preferable to use as a host a mammal cell (monkey COS-7 cell, Chinese hamster CHO cell, human HeLa cell and the like) and an insect cell (*Spodoptera frugiperda* SF9, SF21 and the like).

The vector can be appropriately selected depending upon the expression system used. In the case of the expression system of a mammal cell, a retroviral vector, a papilloma virus vector, a vaccinia virus vector, an SV40 derivative vector and the like can be used. In the case of the expression system of an insect cell, a baculovirus vector and the like can be used.

The promoter for expressing the polypeptide of the present invention can be appropriately selected depending upon the expression system used. In the expression system of a mammal cell, SV40 promoter, LTR promoter, elongation 1α promoter and the like can be used. In the case of the expression system of an insect cell, polyhedrin promoter and the like can be used.

As the nucleic acid encoding the polypeptide of the present invention, there can be used, but not being limited thereto, a cDNA corresponding to a naturally occurring mRNA (for instance, cDNA having the nucleotide sequence shown in SEQ ID NO: 8). A DNA which is designed to be generated as a DNA corresponding to an amino acid sequence of the desired polypeptide can be used. In this case, as a codon encoding one amino acid, 1 to 6 kinds of codons each have been known. The codon used may be arbitrarily selected. For instance, by taking into consideration the codon usage frequency by a host utilized in expression, a sequence showing an even higher expression efficiency can be designed. The DNA having the designed nucleotide sequence can be obtained by chemical synthesis of a DNA, partial modification of the nucleotide sequence and the like. The artificial modification of a part of a nucleotide sequence, and mutation can be carried out by PCR method utilizing primers each consisting of a synthetic oligonucleotide encoding the desired modification, site specific mutagenesis (Mark et al., *Proceedings of National Academy of Sciences*, 81, 5662-5666, 1984), and the like.

The isolation and purification of the polypeptide of the present invention can be carried out by appropriately combining the known purification methods (salting-out with an inorganic salt, fractionation precipitation with an organic solvent, ion-exchanging resin column chromatography, affinity column chromatography, gel filtration and the like) from a culture of a cell into which an expression vector is introduced and the like.

In addition, the antibody capable of recognizing the polypeptide of the present invention can be obtained by using as an antigen the polypeptide of the present invention or a peptide having immunological equivalence thereto (synthetic peptide having a fragment of the polypeptide or a partial sequence thereof and the like). Having immunological equivalence as used herein means, for instance, the generation of cross-reaction with an antibody against the polypeptide of the present invention.

The polyclonal antibody can be produced by a usual method comprising inoculating an antigen to a host animal (for instance, rat, rabbit or the like), and then collecting immune serum. The monoclonal antibody can be produced by a technique of a usual hybridoma method or the like. Alternatively, a humanized monoclonal antibody or the like can be produced by modifying a gene of the monoclonal antibody.

Expression of the polypeptide of the present invention in a cell, a tissue or the like can be detected by a usual immunochemical method (immunochemical assay method or the like) using the above-mentioned antibody. Alternatively, the purification of the polypeptide of the present invention can be carried out by affinity chromatography with an antibody. In addition, the function or activity of the polypeptide of the present invention can be changed (for instance, suppressed) by using a neutralizing antibody.

The nucleic acid having a high sequence homology as compared to the nucleic acid of the present invention, and the nucleic acid (oligonucleotide or polynucleotide) capable of hybridizing with the nucleic acid of the present invention under stringent conditions, or a complement thereof can be used as (A) a probe or a primer for detecting expression or the presence of a gene consisting of the nucleic acid of the present invention by applying a conventional technique in this field of art. Alternatively, there can be used as, for instance, (B) an antisense oligonucleotide, a ribozyme or decoy, for changing (for instance, suppress) expression of a gene consisting of the nucleic acid of the present invention by applying a conventional technique in this field of art. The nucleic acid or a complement thereof as described above includes, for instance, a nucleotide having a partial sequence of 14 or more consecutive nucleotides of the nucleic acid (sense strand or antisense strand) having the nucleotide sequence shown in SEQ ID NO: 8, or a complementary sequence thereof.

In addition, the function or activity of the polypeptide in a cell can be increased (enhanced) by overexpression of the polypeptide of the present invention.

The presence of a phospholipase $A_2$ activity of the polypeptide of the present invention can be confirmed, for instance, by a known method for measuring a phospholipase $A_2$ activity (Underwood et al., *The Journal of Biological Chemistry*, 273, 21926-21932, 1998, and the like).

As the substrate for the enzymatic reaction, a glycerophospholipid such as 1-palmitoyl-2-arachidonyl-phosphatidylcholine can be used.

In addition, the action of a test substance on the phospholipase $A_2$ comprising the polypeptide of the present invention can be evaluated by using the polypeptide, so that the polypeptide can be used for characterizing, identifying or screening an inhibitor.

For instance, the action of the test substance on the phospholipase $A_2$ comprising the polypeptide of the present invention can be assayed by contacting the phospholipase $A_2$ with the test substance.

The assay for the action of a test substance can be carried out, for instance, by:
   carrying out an enzymatic reaction in a reaction system containing a phospholipase $A_2$ comprising the polypeptide of the present invention, a substrate for the phospholipase $A_2$ (a glycerophospholipid) and a test substance, to assay an inhibitory action of the test substance on an enzyme activity of the phospholipase $A_2$ (an activity of hydrolyzing an ester bond of a glycerophospholipid at 2-position) (referred to as Embodiment I); or
   carrying out a binding reaction in a reaction system containing a phospholipase $A_2$ and a test substance to assay a binding activity between the phospholipase $A_2$ and the test substance (referred to as Embodiment II).

There is a high possibility that a test substance (ligand) having a binding activity to a phospholipase $A_2$ comprising the polypeptide of the present invention is used as an inhibitor.

In the above-mentioned Embodiment I, the inhibitory action can be assayed by comparing an enzyme activity $A_0$ in the reaction in the absence of the test substance with an enzyme activity $A_1$ in the reaction in the presence of the test substance. The case of $A_0 > A_1$ is used as an index that the test substance has an inhibitory action.

In addition, in the above-mentioned Embodiment II, the binding activity can be assayed by surface plasmon analysis and the like. For instance, when analyzed by surface plasmon analysis, the binding can be assayed by supplying at a given flow rate a solution containing a test substance to a sensor chip in which the phospholipase $A_2$ of the present invention is immobilized, and detecting the presence or the absence of binding, a binding rate or the like as an optical change or a mass change with an appropriate detection means [for instance, a combination of optical detection (fluorescence, fluorescence polarization and the like), and a mass spectrometer (matrix-assisted laser desorption ionization time-of-flight mass spectrometer: MALDI-TOF MS, electrospray ionization mass spectrometer: ESI-MS and the like)]. Here, the case where sensorgram indicating the formation of a complex of a phospholipase $A_2$ with a test substance, for instance, an optical sensorgram or mass sensorgram, is changed by introduction of the test substance by supplying is used an index that the phospholipase $A_2$ binds to the test substance. Also, the faster the formation of the complex is, it is an index that the test substance has a high binding affinity to the phospholipase $A_2$.

Further, the selectivity of the inhibitory action (or the binding activity) can be judged by evaluating the inhibitory action (or the binding activity) on the polypeptide (phospholipase $A_2$) of the present invention for a test substance (preferably a low-molecular compound or the like), and comparing with an inhibitory action (or binding activity) on other types of phospholipase $A_2$. By the judgment, an inhibitor having a relatively high action on a particular type of the phospholipase $A_2$ (selective inhibitor) can be screened. In addition, the inhibitor can be identified and characterized.

The above-mentioned "other types of phospholipase $A_2$" include, for instance, cPLA$_2\alpha$ (GenBank Ac. No. M72393; Clark et al., *Cell*, 65, 1043-1051, 1991); cPLA$_2\beta$ (GenBank Ac. No. AF065215; Pickard et al., *The Journal of Biological Chemistry*, 274, 8823-8831, 1999); cPLA$_2\gamma$ (GenBank Ac. No. AF058921; Underwood et al., *The Journal of Biological Chemistry*, 273, 21926-21932, 1998); and the like. The above-mentioned cPLA$_2\alpha$, cPLA$_2\beta$, cPLA$_2\gamma$ and the like may be used in accordance with the reaction conditions described in the literature of Clark et al., the literature of Pickard et al., and the literature of Underwood et al. mentioned above depending upon each of the enzymes.

The polypeptide of the present invention is a phospholipase $A_2$ of which expression is increased in epidermis of a patient with psoriasis. As described above, the phospholipase $A_2$ is an enzyme which plays a key role in the production of an inflammatory mediator. Therefore, the inhibitor for the phospholipase $A_2$ of the present invention (compound capable of inhibiting the phospholipase) is expected to have an effect as an active ingredient of a medicament (therapeutic agent or the like) in the treatment of an inflammatory dermal disease (especially a chronic intractable dermal disease such as psoriasis) or the like.

Therefore, the polypeptide of the present invention can be used for characterizing, identifying or screening a therapeutic agent for an inflammatory dermal disease. In other words, there can be carried out characterization, identification or screening of a therapeutic agent for an inflammatory dermal disease (for instance, a chronic intractable dermal disease such as psoriasis) by assaying an action of a test substance on a phospholipase $A_2$ comprising the polypeptide of the present invention, and determining inhibition (desirably selective inhibition) of the phospholipase $A_2$.

Also, the pharmaceutical composition for treatment of an inflammatory dermal disease (for instance, a chronic intractable dermal disease such as psoriasis) can be prepared by mixing together with a carrier a test substance by which inhibition (desirably selective inhibition) for the phospholipase $A_2$ has been determined.

In addition, the test substance by which inhibition (desirably selective inhibition) for the phospholipase $A_2$ has been determined, or a composition containing this test substance, can be sold as a useful medicament, especially a therapeutic agent for an inflammatory dermal disease (for instance, a chronic intractable dermal disease such as psoriasis).

In addition, the phospholipase $A_2$ in human can be inhibited by administering to a human individual who is a patient with an inflammatory dermal disease (for instance, a chronic intractable dermal disease such as psoriasis), a test substance of which action on the phospholipase $A_2$ comprising the polypeptide of the present invention has been assayed to determine inhibition (desirably selective inhibition) of the phospholipase $A_2$.

Here, as the test substance, the use of a compound which has not been known to inhibit phospholipase $A_2$ leads to generation of a novel medicament, specifically, a therapeutic agent for an inflammatory dermal disease and a method of treatment therefor.

By administering an effective dose of a compound capable of inhibiting (desirably selectively inhibiting) the phospholipase $A_2$ to a patient, the inflammatory dermal disease (for instance, a chronic intractable dermal disease such as psoriasis) can be treated. The pharmaceutical composition comprising as an active ingredient a compound capable of inhibiting (desirably selectively inhibiting) the phospholipase $A_2$ is useful for the treatment of an inflammatory dermal disease (for instance, a chronic intractable dermal disease such as psoriasis).

The inhibitor on the phospholipase $A_2$ of the present invention (compound capable of inhibiting the phospholipase $A_2$ of the present invention) includes a compound having $IC_{50}$ value of usually 30 µM or less, preferably 10 µM or less, more preferably 1 µM or less, when determined in the same manner as in Examples set forth below.

In addition, it is desirable to use a selective inhibitor on the phospholipase $A_2$ of the present invention (compound capable of selectively inhibiting the phospholipase $A_2$ of the present invention) as the compound serving as an active ingredient, from the viewpoint of reducing side effects when used as a medicament. In other words, among the compounds capable of inhibiting the phospholipase $A_2$ of the present invention, it is desirable to use a compound which has 3-folds or more, preferably 10-folds or more potent inhibitory action on the phospholipase $A_2$ of the present invention, as compared to inhibitory actions on the other types of the phospholipase $A_2$ ($cPLA_2\alpha$, $cPLA_2\beta$, $cPLA_2\gamma$ and the like).

The anti-inflammatory action possessed by the inhibitor on the phospholipase $A_2$ of the present invention can be evaluated and confirmed by a known method for assaying an anti-inflammatory action or a method equivalent thereto.

For instance, the anti-inflammatory action possessed by the test substance can be assayed and evaluated by administering a test substance to an inflammatory model of a mammal. As the inflammatory model, a known model can be used. For instance, as the psoriatic model, there can be used a model generated by transplanting a skin of a psoriatic patient to an immunodeficient mouse (nude mouse, SCID mouse) [Fraki J. E. et al., *J. Invest. Dermatol.*, 80, 31s-35s, 1983; Nickoloff B. J. et al., *Am. J. Pathol.*, 146, 580-588, 1995]; a model generated by injecting T cells to the same mouse [Schon M. P. et al., *Nature Med.*, 3, 183-188, 1997]; and the like. Here, the case where a transplanted skin on an inflammatory model exhibits, for instance, disappearance or atrophy of scale or erythema by the administration of a test substance is used an index that the test substance has an anti-inflammatory action. In addition, the extent of the anti-inflammatory action can be judged, for instance, by using as an index an extent of alterations of expression of a differentiation marker for keratinocyte (K5, K10) on a transplanted skin from a psoriatic pathology type to a normal type.

The method of administering an inhibitor on the phospholipase $A_2$ of the present invention is not particularly limited, and a general oral or parenteral method (oral, intravenously, intramuscular, subcutaneous or the like) may be applied. In addition, there may be formulated into a conventional pharmaceutical preparation (tablet, granule, capsule, powder, injectable, inhalant or the like), together with an inert carrier depending upon the administration method if needed and used. For instance, the inhibitor can be used by formulation into a preparation by a usual method together with an excipient or diluent, such as a binder, a disintegrating agent, an extender, a filler, or a lubricant, which is acceptable in a general medicament.

The dose differs depending upon the administration method, and age, weight and conditions of a patient, and a general dose per day is set, for instance, within the range of 0.01 to 300 mg/kg.

The pharmaceutical composition for treating an inflammatory dermal disease of the present invention, comprising an inhibitor for the phospholipase $A_2$ of the present invention as an active ingredient exhibits pharmacological efficacy (anti-inflammatory action) based on the inhibitory action on the phospholipase $A_2$ of the present invention. Therefore, a medicament exhibiting a pharmacological efficacy based on a main action other than the phospholipase $A_2$ inhibition is not encompassed in the present invention.

Also, the gene encoding the polypeptide of the present invention, that is, the gene consisting of the nucleic acid of the present invention is a gene of which expression is increased in a psoriatic tissue as compared to a normal tissue. Therefore, the pathological conditions of psoriasis, and the like can be diagnosed or assayed by testing an expression level of the gene in a biological sample.

Therefore, according to the present invention, a method for examining psoriasis is also provided.

The examination method of the present invention is a method characterized by testing an expression level of a gene encoding the polypeptide of the present invention for a biological sample collected from a human or non-human animal individual.

According to the examination method of the present invention, there can be utilized in, for example, judgment of whether or not an individual suffers from psoriasis, judgment on the characteristics of pathological conditions of psoriasis, judgment on severity of psoriasis, or judgment on the effect of a therapeutic agent or a method of treating on psoriasis. Inter alia, the examination method of the present invention is preferably applied to psoriasis vulgaris. In addition, the examination method of the present invention can be applied to a psoriatic model of a mammal such as monkey, dog, rat and mouse, besides the application to human psoriasis. Further, according to the method for examining psoriasis of the present invention, there can be enabled to examine psoriasis simply, rapidly and in an excellent sensitivity and to detect a psoriatic tissue.

Conventionally, psoriasis has been mainly empirically diagnosed by a physician from a pathological tissue image. However, according to the examination method of the present invention, there can be carried out an objective diagnosis using an expression level of the gene of the present invention as an index.

The examination method of the present invention is carried out by collecting and preparing a biological sample from a human or non-human animal individual (an individual suffering from psoriasis, an individual being suspected of suffering from psoriasis and the like), and thereafter assaying an expression level of the gene using this biological sample.

Concretely, the examination method of the present invention is carried out by:

assaying the above-mentioned expression level using as a probe or a primer a nucleic acid capable of hybridizing with a nucleic acid having the nucleotide sequence shown in SEQ ID NO: 8 under stringent conditions, or a complement thereof; or assaying the above-mentioned expression level using an antibody capable of recognizing the polypeptide of the present invention.

The biological sample includes a cell, a tissue, and the like, derived from an animal (human or non-human) individual. The tissue includes a skin tissue, and especially a skin tissue at a psoriatic lesion site such as scale is preferable. The cell includes an epidermic cell existing in the skin tissue or the like.

The assay for the expression level of the gene in a biological sample can be carried out, for instance, by extracting mRNA from a biological sample to detect or assay mRNA derived from the gene existing in this mRNA (or corresponding cDNA). Alternatively, the polypeptide of the present invention which is a gene product of the gene may be detected or assayed.

In the detection or the assay of mRNA (or corresponding cDNA) from the gene, RT-PCR (reverse transcriptase-polymerase chain reaction) method ("*PCR Protocols*" Innis M H, Gelfad D H, Sninsky JJ and White T J eds., Academic Press, San Diego, 1990); iAFLP method utilizing RT-PCR method (Kawamoto et al., *Genome Research,* 9, 1305-1312, 1999); DNA microarray method or DNA microchip method (Schena et al., *Science,* 270, 467-470, 1995; Fodor et al., *Science,* 251, 767-773, 1991), usual Northern blotting method and the like can be utilized.

Among them, the RT-PCR method is preferable from the viewpoints of sensitivity and operability. Also, the iAFLP method utilizing the RT-PCR method is a method which is made high-throughput more effectively than the RT-PCR method, and is preferable for assaying a large number of samples.

For instance, when the RT-PCR method is utilized, appropriate primers for amplifying a fragment containing a region having a specific nucleotide sequence in mRNA (or a corresponding cDNA) from the gene are designed and synthesized. Using these primers, PCR is carried out with a cDNA synthesized from mRNA in a biological sample as a template. The resulting PCR product is separated by electrophoresis if needed, and a fragment thereof may be detected to assay the existing amount thereof.

In the detection and the assay of mRNA (or a corresponding cDNA), usually, a nucleic acid (oligonucleotide or the like) capable of hybridizing with a region having a specific nucleotide sequence among mRNA (or corresponding cDNA) from the gene, or a complement thereof is designed and synthesized, and this is used as a probe or a primer.

The region having a specific nucleotide sequence is not particularly limited. Since a region on a 3'-terminal side of mRNA (or a corresponding cDNA) has a high sequence specificity in the individual genes, it is preferable to employ a probe or a primer corresponding to this region from the viewpoint that the gene expression level is appropriately reflected in the detection or assay. The region on a 3'-terminal side in a gene comprising the nucleic acid of the present invention includes, for instance, a region from polyA to MboI recognizing site appearing first upstream therefrom in mRNA of the GS21015 gene, concretely, a region having the nucleotide sequence shown in SEQ ID NO: 4.

When expression of the gene comprising the nucleic acid of the present invention is detected or assayed by detecting the polypeptide of the present invention, which is the gene product, for instance, an antibody which is capable of specifically recognizing the polypeptide of the present invention is produced by the above-mentioned method, and a method of detection by the usual immunochemical method can be used utilizing this antibody.

Alternatively, a psoriatic tissue can be detected by evaluating expression of the nucleic acid or the polypeptide of the present invention in a biological sample in a means similar to those described above.

The present invention will be described hereinafter more specifically by means of Examples, without intending to limit the present invention to these Examples.

In the following Examples, unless specified otherwise, each of the procedures was carried out in accordance with the method described in "*Molecular Cloning*" (authored by Sambrook, J., Fritsch, E. F. and Maniatis, T., published on 1989 by Cold Spring Harbor Laboratory Press), or by using an instruction manual of a commercially available product when a commercially available reagent or kit is used.

EXAMPLE 1

Profiling of Psoriasis-Associated Gene by Body Map Method

Random screening of a psoriasis-associated gene was carried out by Body Map method, in accordance with the method described in the literature of Okubo et al. (*Methods in Molecular Genetics,* 5, 17-33, 1994), as follows.

(1) Preparation of Vector Primer

A vector plasmid pUC119 (manufactured by TAKARA BIO INC.) was digested with restriction enzyme PstI, and thereafter the digested product was reacted with [$^3$H]dTTP and terminal transferase to add oligo dT (about 30 to 35 in number) to the terminal. There was used a vector plasmid pUC119 which had been prepared by replicating and preparing the vector plasmid using dam+ bacterium (strain name: *Escherichia coli* DH5α; manufactured by Toyobo Co., Ltd.) as a host so as not to be digested with restriction enzyme MboI. The state for addition of oligo dT was monitored by radioactivity of incorporated [$^3$H]dTTP. Subsequently, the resulting vector was digested with HincII. Thereafter, the digested product was extracted with phenol-chloroform and precipitated by ethanol for several times. Further, a longer vector fragment was purified and obtained using oligo(dA) cellulose column. This vector fragment was used as a primer (vector primer).

(2) Preparation of 3'-Oriented cDNA Library and Determination of Nucleotide Sequence of Each Clone Each of one case of a skin tissue (scaly skin tissue of lesion site) collected from a psoriatic patient and one case of a skin tissue collected from a normal individual was physically disrupted in Cool Mill (manufactured by Toyobo Co., Ltd.). Thereafter, a total RNA was prepared from these samples using RNA preparation kit (RNeasy kit, manufactured by QIAGEN).

With the thus obtained total RNA (about 1 μg each) (derived from a psoriasis patient or a normal individual) as a template, a single-stranded cDNA was synthesized from a 3' side of the template, using 50 ng of the vector primer prepared in the above (1) as a primer, and reverse transcriptase (trade name: Superscript II; manufactured by BRL) of MMLV (Moloney murine leukemia virus). Thereafter, a double-stranded cDNA was synthesized using polymerase, ligase, and the like. Further, a cDNA was purified and obtained using Glass Milk (manufactured by BIO 101) (or by extraction with phenol-chloroform and ethanol precipitation).

The resulting double-stranded cDNA (the one added to vector) was digested with restriction enzyme MboI (recognizing GATC sequence) and BamHI. The digested product was then ligated with MboI adapter, and thereafter a fragment containing a vector was circularized. The resulting product was introduced into *Escherichia coli* (strain name: *Escherichia coli* DH5α; manufactured by Toyobo Co., Ltd.) to give a transformant.

A colony of the resulting transformant (about 10000 each for the clones derived from tissues of normal individuals and from psoriatic patients) was picked up on a 96-well plate using an automatic bacterium-picking up device. The cells were cultured on the 96-well plate, and thereafter heated in an autoclave (90° C. for 20 minutes) to lyse the cells. The cell lysate was filtered with Millipore filter to obtain supernatant. PCR was carried out using the resulting supernatant as a template to amplify an insert in a vector plasmid. PCR was carried out for 27 cycles under the conditions that one cycle comprises 93° C. for 30 seconds, 50° C. for 60 seconds and 72° C. for 2 minutes, followed by one cycle under the conditions of 72° C. for 5 minutes as a final cycle, and thereafter the reaction was terminated. In addition, the primers for PCR were designed on the basis of a nucleotide sequence of a vector part nearby the insert. As a sense primer, there was used oligonucleotide (FW(-40)) having the nucleotide sequence shown in SEQ ID NO: 1, and as an antisense primer, there was used oligonucleotide (RV(-14)) having the nucleotide sequence shown in SEQ ID NO: 2, in the Sequence Listing set forth below.

Next, the PCR product obtained above was subjected to a sequencing reaction in accordance with the dideoxy method, and thereafter a nucleotide sequence was determined using an automatic DNA sequencer (373A, manufactured by Applied Biosystems). As a primer for a sequencing reaction, there was used an oligonucleotide of the nucleotide sequence shown in SEQ ID NO: 3 from a vector (vector primer).

Thus, 10000 each of cDNA clones from normal and psoriatic skin tissues were subjected to nucleotide sequencing, and clones for which nucleotide sequences could not be decoded and clones from mitochondria were removed. As a result, the nucleotide sequence information of about 4300 clones from normal tissues and about 3700 clones from psoriatic tissues was obtained. As the kinds of genes expressed in human skin tissues (psoriatic and normal), the genetic information of a total of about 3000 kinds was obtained.

Among the genetic information obtained above, the information on the cDNA sequence obtained for clone GS21015 (i.e. a nucleotide sequence from polyA at 3'-terminal of cDNA to MboI site appearing first) is as shown in SEQ ID NO: 4 in the Sequence Listing set forth below.

EXAMPLE 2

Analysis of Expression Profile by iAFLP Method

As to the clones obtained in Example 1 mentioned above, a difference in expression profile between the psoriatic tissues and the normal tissues was analyzed by iAFLP (introduced amplified fragment length polymorphism) method utilizing RT-PCR (reverse transcriptase-polymerase chain reaction) in accordance with the method described in the publication of Kawamoto et al. (*Genome Research*, 9, 1305-1312, 1999).

First, a total RNA was prepared from each of 10 cases of skin tissues collected from psoriatic patients (scaly skin tissue of lesion site) (referred to as P01, P02, P03, ..., P10), and 7 cases of skin tissues collected from normal individuals (referred to as N01, N02, N03 ..., N07).

A 3'-side double-stranded cDNA (the one added to the vector) was obtained by carrying out the treatment in the same manner as that of the above (2) of Example 1 using the resulting RNA as a template and the vector primer prepared in the above (1) of Example 1 for PCR. The thus obtained 3'-side double-stranded cDNA (added to the vector) was used hereinbelow as a cDNA pool derived from each tissue.

A total amount of each of the cDNA pools obtained above was digested with a restriction enzyme MboI (recognizing GATC sequence), and thereafter an amplification adapter was ligated to each of the digested products. Five kinds of adapters which are different in a length by 3 bases each (LP40, LP43, LP46, LP49, and LP52) were used as the amplification adapters, in the following combinations so that PCR products can be distinguished even when subjected to simultaneous treatment.

| | |
|---|---|
| P01, P06, N01, N06 | → ligated with LP40 (40 bases in length) |
| P02, P07, N02, N07 | → ligated with LP43 (43 bases in length) |
| P03, P08, N03 | → ligated with LP46 (46 bases in length) |
| P04, P09, N04 | → ligated with LP49 (49 bases in length) |
| P05, P10, N05 | → ligated with LP52 (52 bases in length) |

In addition, as a standard (reference), a mixture of 30 kinds of commercially available cDNA libraries from human organs was used in place of each of the cDNA pools, and a 6th kind of the amplification adapter (LP55; 55 bases in length) was ligated thereto.

PCR was carried out with the cDNA ligated with amplification adapters as mentioned above as a template. As the sense primer for PCR, there was used a fluorescent-labeled oligonucleotide (F-T7(25) primer, manufactured by PE Biosystems) (2 pmole) having a common nucleotide sequence to the 6 kinds of amplification adapters. As the antisense primer, there was used an oligonucleotide (2 pmole) designed and synthesized on the basis of a sequence which is unique to a gene (clone) of which expression level is to be detected (i.e., a specific sequence in the nucleotide sequence from 3'-terminal polyA of cDNA to MboI site appearing first). Concretely, as an antisense primer for detecting gene expression of clone GS21015, an oligonucleotide having the nucleotide sequence shown in SEQ ID NO: 5 was used.

Equivolumes of 3 to 5 kinds of templates ligated with different kinds of amplification adapters, and a standard template in one reaction solution (10 μl) as follows were mixed, and thereafter PCR was carried out.

Reaction solution 1=N01, N02, P03, P04, P05, and standard

Reaction solution 2=N03, N04, P01, P02, P06, and standard

Reaction solution 3=N05, N06, P07, P08, and standard

Reaction solution 4=N07, P09, P10, and standard

The reaction for PCR was carried out for 35 cycles under the conditions that one cycle comprises 94° C. for 30 seconds, 55° C. for 30 seconds and 72° C. for 30 seconds, followed by one cycle under the conditions of 72° C. for 30 seconds as a final cycle, and thereafter the reaction was terminated.

The resulting PCR product was electrophoresed using ABI automatic sequencer (manufactured by ABI) to detect and quantify the fluorescent light.

As to the detection value ascribed to the cDNA pool of each tissue sample, a relative value was calculated to a detected value ascribed to the standard cDNA, and this value was defined as a relative value of an expression level of a gene (transcript) in each tissue sample.

As mentioned above, the gene expression profile of the clone GS21015 was analyzed. The results are as shown in FIG. 1.

The gene corresponding to the clone GS21015 (GS21015 gene) showed a higher expression level in a skin tissue from a psoriatic patient as compared to those in a skin tissue from a normal individual. Since the GS21015 gene shows an expression profile specific to a psoriatic patient tissue, it was found that the gene can be used for diagnosing or examining pathological conditions of psoriasis.

EXAMPLE 3

Cloning of GS21015 Gene (Full Length cDNA)

As to the clone GS21015 of which a gene expression profile was confirmed in Example 2 mentioned above, a cDNA containing a full length translation region was obtained as follows.

The known DNA database (GenBank and EMBL) were searched using BLAST program on the basis of the sequence information obtained in Example 1 (cDNA nucleotide sequence from 3'-terminal of polyA to MboI site appearing first: SEQ ID NO: 4). Conditions for searching were open gap penalty 5, extend gap penalty 2, and word length 11.

As a result, the sequence was hit with a genome draft sequence. Exon was extracted from this draft sequence using an exon extraction software (GeneScan), and translated into an amino acid sequence, and then searched for protein database (NBRF and SWISS-PROT) by using the amino acid sequence. As a result, the exon showed a high homology with a particular region of cytoplasmic phospholipase $A_2$ (cPLA$_2$).

PCR primers (one having the nucleotide sequence shown in SEQ ID NO: 6 and one having the nucleotide sequence shown in SEQ ID NO: 7) were designed on the basis of this hypothetical exon information. PCR was carried out using these primers, to obtain a 3'-terminal cDNA fragment (1246 bp) of the GS21015 gene of a cDNA from a psoriatic tissue.

Further, a cDNA library from a psoriatic tissue was screened using this cDNA fragment as a probe. As the cDNA library, there was used one prepared by inserting into λZap vector a cDNA synthesized with mRNA prepared from a skin tissue (scaly skin tissue of lesion site) of a psoriatic patient as a template. As a result of screening, a full length cDNA containing a full length translation region of the GS21015 gene was obtained.

The resulting full length cDNA was sequenced and analyzed. The nucleotide sequence (3587 bp) of the full length cDNA was shown in SEQ ID NO: 8, and the amino acid sequence (818 amino acid residues) of a protein encoded thereby was shown in SEQ ID NO: 9. The molecular weight of a protein deduced from the amino acid sequence was about 92 kDa.

In addition, as to the nucleotide sequence shown in SEQ ID NO: 8, all the sequences contained in the known DNA database (GenBank and EMBL) were subjected to homology searching using FASTA and BLAST programs. Further, as to the amino acid sequence shown in SEQ ID NO: 9, all the sequences contained in the protein database (NBRF and SWISS-PROT) were subjected to homology searching using FASTA and BLAST programs. Conditions for searching of the nucleotide sequence were open gap penalty 5, extend gap penalty 2, and word length 11. The conditions for searching for the amino acid sequence were open gap penalty 11, extend gap penalty 1, and word length 3.

As a result of homology searching and analysis, it was found that the amino acid sequence shown in SEQ ID NO: 9 has partial homology with an amino acid sequence of cytoplasmic phospholipase $A_2$ (cPLA$_2$).

Figure 2:
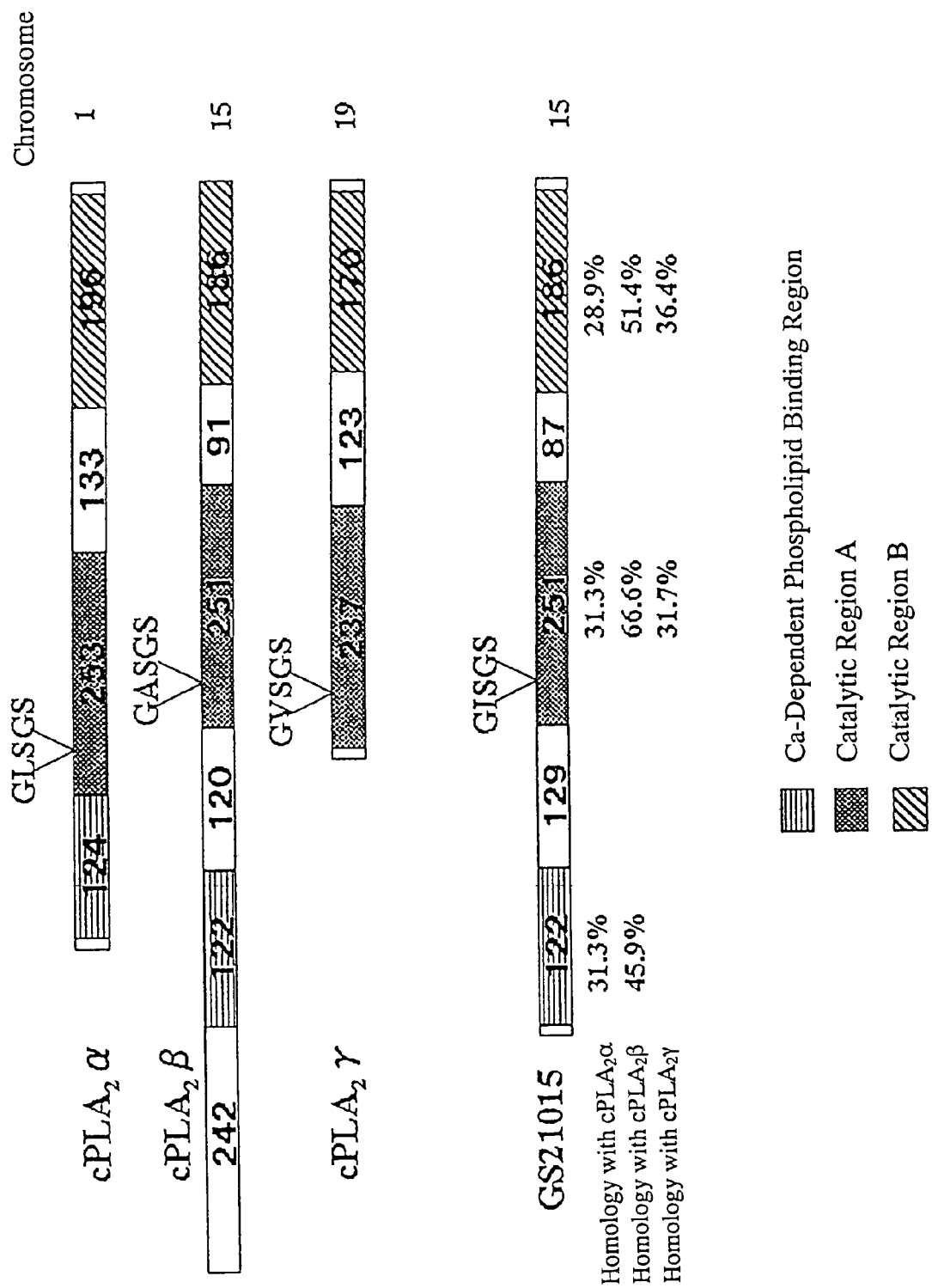
FIG. 2 is a diagram showing homology obtained by comparing an amino acid sequence of GS21015, and amino acid sequences of cPLA$_2$α, cPLA$_2$β and cPLA$_2$γ which have conventionally been known as molecular species of cPLA$_2$.

The amino acid sequence of GS21015 shown in SEQ ID NO: 9, and amino acid sequences of cPLA$_2$α, cPLA$_2$β and cPLA$_2$γ, which have been conventionally known as molecular species of cPLA$_2$, were compared. The results are shown in FIG. 2.

From the similarity of the amino acid sequences, it was deduced that a catalytic region of GS21015 is a region corresponding to 275th to 525th amino acid residues (catalytic region A) and 613th to 798th amino acid residues (catalytic region B). In addition, it was deduced that GS21015 has a phospholipid binding region at N-terminal side (region corresponding to 24th to 145th amino acid residues), and is capable of binding to a phospholipid membrane in a $Ca^{2+}$ concentration-dependent manner, in the same manner as in cPLA$_2$α and cPLA$_2$β.

When the amino acid sequence of GS21015 was compared with the amino acid sequences of cPLA$_2$α, cPLA$_2$β and cPLA$_2$γ, in the catalytic region A, there were shown homologies of 31.3% for cPLA$_2$α, 66.0% for cPLA$_2$β and 31.7% for cPLA$_2$γ, and in the catalytic region B, there were shown homologies of 28.9% for cPLA$_2$α, 51.4% for cPLA$_2$β and 36.4% for cPLA$_2$γ. In the phospholipid binding region, there were shown homologies of 31.3% for cPLA$_2$α, and 45.9% for cPLA$_2$β. In the full length of the amino acid sequence, there were shown homologies of 29.3% for cPLA$_2$α, 50.3% for cPLA$_2$β and 27.8% for cPLA$_2$γ.

It was deduced from the results of the comparison and analysis of these amino acid sequences that GS21015 is a member of the family of cPLA$_2$, and inter alia, a molecular species which is closest to cPLA$_2$β.

In addition, it was found from the information of the genome draft sequence that the GS21015 gene is localized on chromosome 15, the same as cPLA$_2$β.

EXAMPLE 4

Overexpression of GS21015

The GS21015 gene (full length cDNA) obtained in Example 3 mentioned above was amplified by PCR. In the amplification, as PCR primers there were used primers which were designed so that EcoRI recognition site was added to each of 5'-terminal and 3'-terminal of the cDNA fragment.

Next, the resulting PCR product (cDNA fragment containing full length translation region of GS21015) was inserted into EcoRI recognition site of vector plasmid pcDNA4 His-Max (manufactured by Invitrogen), thereby constructing an expression vector plasmid for GS21015. This expression vector plasmid is constructed so as to express a protein in which histidine (His) tag was added to the N-terminal of GS21015.

COS-7 cells (Riken RCB0539) were plated in a concentration of 2×10$^6$ cells/10 cm dish, and cultured overnight. Ten micrograms of the expression vector plasmid constructed as mentioned above (or vector plasmid pcDNA4 HisMax as control) was transfected into COS-7 cells using together with lipofection reagent (trade name: SuperFect, manufactured by Qiagen), and thereafter the transfected cells were cultured for additional 48 hours.

Using the cells after the culture, overexpressed GS21015 (N-terminal, His tagged) was detected by Western blotting method as follows. Concretely, the cells after the culture were harvested, and thereafter 500 μl of buffer (10 mM HEPES pH 7.5, 1 mM EDTA, 0.34 M sucrose, 1 mM PMSF, 0.1 M DTF)

was added thereto to lyse the cells. The cell lysate was centrifuged (15000 rpm for 15 minutes). After supernatant was taken, a 10 μl portion thereof was subjected to SDS-polyacrylamide gel electrophoresis.

Next, the electrophoresed protein was transferred to a PVDF membrane (trade name: Immobilon-P membrane, manufactured by Millipore) by semi-dry method. Thereafter, the membrane was immersed overnight at 4° C. in a solution containing a blocking reagent (Blockace, manufactured by Dainippon Pharmaceutical Co., Ltd.), thereby blocking the membrane. Further, the blocked membrane was reacted with anti-His tag antibody (manufactured by Qiagen) (1000-fold dilution) at room temperature for 2 hours, and thereafter the reaction product was washed with PBS-Tween (trade name) [phosphate buffered physiological saline containing 0.1% Tween (trade name)]. Subsequently, the membrane was reacted with peroxidase-labeled anti-mouse IgG antibody (manufactured by Sigma) at room temperature for 2 hours. Furthermore, a protein band bound to the anti-His tag antibody in the membrane was detected using a color developing reagent (trade name: ECL System, manufactured by Amersham).

As a result, a main positive band was recognized around a molecular weight of about 97 kD corresponding to tagged GS21015.

EXAMPLE 5

Analysis of Enzymatic Characteristics of GS21015 and Enzyme Assay (1) Determination of Phospholipase $A_2$ Activity of GS21015

The phospholipase $A_2$ activity of GS21015 was determined as follows:

Supernatant of the cell lysate was obtained from cells overexpressing GS21015 (COS-7 cells with which the expression vector plasmid for GS21015 was transfected) in the same manner as in Example 4 mentioned above, and the resulting supernatant was used as an enzyme solution. In addition, using 1-palmitoyl-2-arachidonyl-phosphatidylcholine as a substrate, the activity of hydrolyzing this substrate (activity of hydrolyzing an ester bond at 2-position to release arachidonic acid) was determined. In addition, the determination of activity was carried out in the same manner as the method described in the literature (Underwood et al., *The Journal of Biological Chemistry*, 273, 21926-21932, 1998), as follows.

First, 1-palmitoyl-2-[$^{14}$C]arachidonyl-phosphatidylcholine (manufactured by Life Science Products) dried under a nitrogen gas was added to a reaction buffer [10 mM HEPES pH 7.5, 2 mM calcium chloride, 150 mM sodium chloride, 30% glycerol, 1 mg/ml bovine serum albumin (fatty acid-free)] so as to have a concentration of 2 μM. The mixture was stirred, immersed in a bath-type ultrasonic washing machine for 30 minutes, and thereafter stirred again. To 250 μl of this substrate solution was added 10 μl of an enzyme solution (supernatant of cell lysate of COS-7 cells into which the expression vector plasmid for GS21015 was transfected; as a control, supernatant of the cell lysate of the same cells into which only the vector was transfected) to initiate the reaction. After the reaction was carried out while keeping the temperature at 37° C. for 0, 30 or 60 minutes, 1.25 ml of a Dole's reagent (2-propanol:heptane: 1 N sulfuric acid=20:5:1) was added thereto to stop the reaction. Further, 0.1 g of silica gel for column chromatography (manufactured by Fuji Silysia Chemical Ltd.) was added thereto and stirred. Thereafter, 0.75 ml of heptane and 0.75 ml of ion-exchanged water were added thereto. The mixture was stirred for 10 seconds or longer. The upper layer (heptane layer) was taken in an amount of 0.5 ml, and mixed with 5 ml of a scintillation solution. Subsequently, the radioactivity was determined with a scintillation counter.

In addition, the phospholipase $A_2$ activity was determined for GS21015 and the control in the same manner as described above except that 5 mM ethylene glycol bis(2-aminoethyl ether) tetraacetic acid [EGTA] was added as a masking agent for a calcium ion in the above-mentioned reaction buffer.

Figure 3:
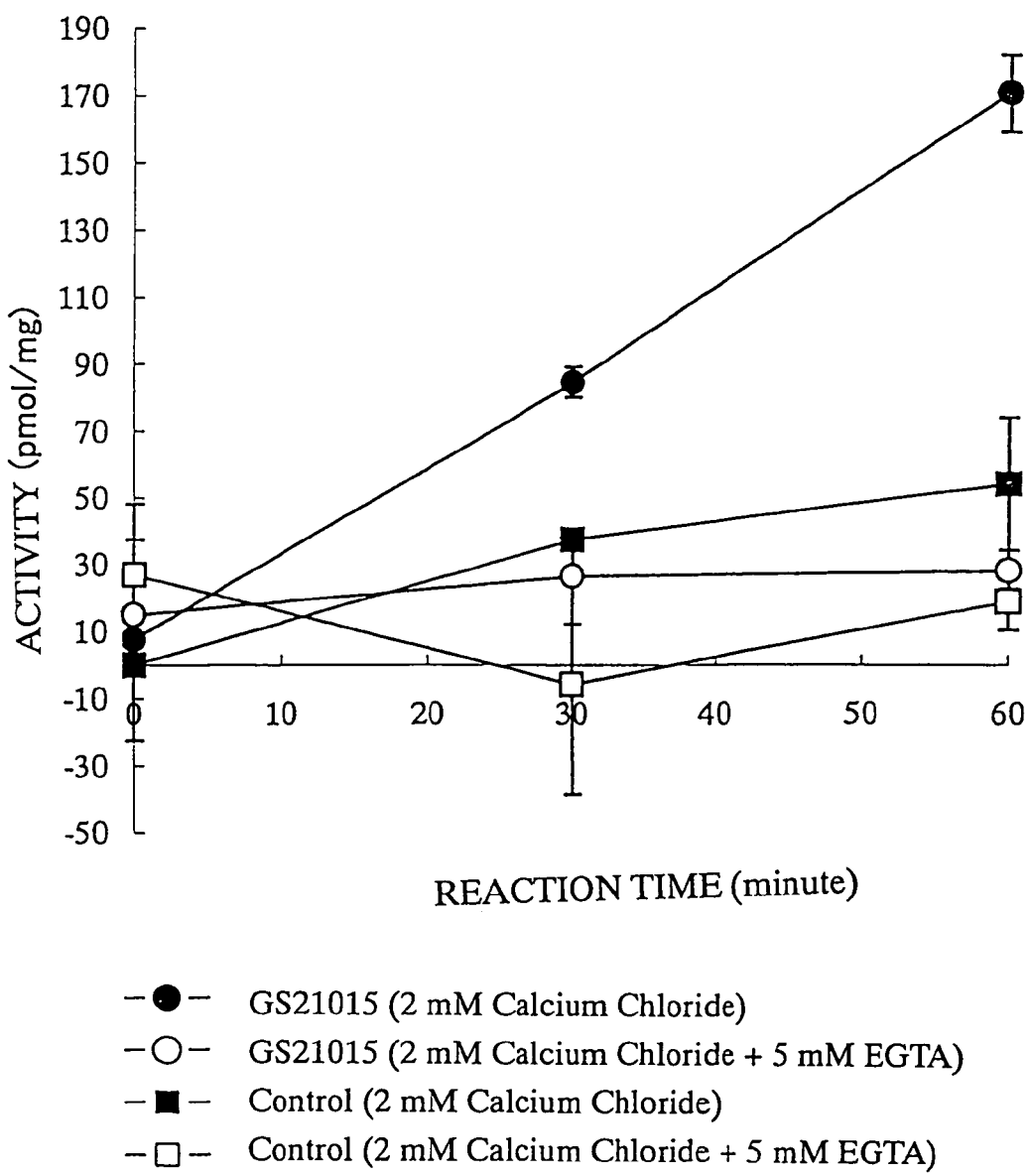
FIG. 3 is a diagram showing correlation between phospholipase A$_2$ activity and reaction time, in each of the case where EGTA (Ca$^{2+}$ masking agent) was not added to a reaction system, and the case where EGTA was added to a reaction system, regarding phospholipase A$_2$ activity of GS21015 (activity of hydrolyzing an ester bond of 1-palmitoyl-2-arachidonyl-phosphatidylcholine at 2-position, to release arachidonic acid).

The results (correlation between the reaction time and the activity) are as shown in FIG. 3. It was made clear that GS21015 has a $PLA_2$ activity in a $Ca^{2+}$ concentration-dependent manner.

(2) Assay for Inhibitory Action of Various Compounds for Phospholipase $A_2$ Activity of GS21015

The phospholipase $A_2$ activity of GS21015 was determined in the presence (or in the absence) of various test substances, and the inhibitory actions by various test substances were evaluated.

The determination of the phospholipase $A_2$ activity of GS21015 was carried out in the same manner as in the above (1), provided that EGTA was not added to the reaction solution, and various test substances (0 to 45 μM) were added thereto.

In addition, the inhibitory action for other type of phospholipase $A_2$ ($cPLA_2\alpha$) was examined in the same manner as described above. An expression vector plasmid for $cPLA_2\alpha$ (GenBank Ac. No. M72393; Clark et al., *Cell*, 65, 1043-1051, 1991) was generated and transfected into COS-7 cells in the same manner as in Example 4. The resulting supernatant of the cell lysate was used as an enzyme solution of $cPLA_2\alpha$.

Coefficients for the inhibitory action assay for the phospholipase $A_2$ activity of GS21015 and $cPLA_2\alpha$ are shown in Table 1 where arachdinyl trifluoromethyl ketone (manufactured by Cayman Chemical) and methyl arachidonyl fluorophosphonate (manufactured by Cayman Chemical) were used as test substances.

TABLE 1

| Inhibitor | $IC_{50}$ Value for GS21015 Activity (μM) | $IC_{50}$ Value for $cPLA_2\alpha$ Activity (μM) |
|---|---|---|
| arachdinyl trifluoromethyl ketone | >45 | <10 |
| methyl arachidonyl fluorophosphonate | <10 | 10-40 |

Among arachdinyl trifluoromethyl ketone and methyl arachidonyl fluorophosphonate, which are inhibitors for $cPLA_2\alpha$, it became to be clear that the latter also has an inhibitory action on the phospholipase $A_2$ activity of GS21015.

EXAMPLE 6

Expression Analysis of GS21015 by in Situ Hybridization

Expression of GS21015 mRNA in the human skin tissue was analyzed by carrying out in situ hybridization using a psoriatic skin tissue and a normal skin tissue from human.

As the probe for in situ hybridization, there was used a cRNA probe obtained as follows. A fragment (nucleotide sequence of the fragment corresponding to a nucleotide sequence of 2522nd to 3236th in the nucleotide sequence shown in SEQ ID NO: 8) of the GS21015 gene (full length cDNA) obtained in Example 3 mentioned above was subcloned into pBluescript vector (manufactured by Stratagene). The resulting plasmid was digested with restriction enzymes XbaI and AccI and transcribed with T7 RNA polymerase and T3 RNA polymerase using the resulting product as a template. In addition, the preparation of a skin tissue section and in situ hybridization were carried out in accordance with the method described in a literature (Shintaro Nomura et al., *Saibokogaku Bessatsu* (9) "*Datsu-aisotopu Jikken Purotokoru* (1) *DIG Haiburidaizeishon* (*Cell Technology Supplement* (9), *De-Isotope Experimental Protocol* (1) *DIG Hybridization*), 72-82, 1994).

The hybridization was carried out under the conditions of incubation at 50° C. for 16 hours in a hybridization solution [composition: 10 mM Tris-HCl (pH 7.6), 0.6 M sodium chloride, 50% formamide, 200 μg/ml tRNA, 1×Denhardt's solution, 0.25% SDS, 1 mM EDTA, 10% dextran sulfate]. The washing was carried out once at 50° C. for 5 minutes with a washing buffer [composition: 5×SSC], and thereafter once at 50° C. for 30 minutes in a washing buffer [composition: 0.2×SSC, 50% formamide].

As a result, it was found that GS21015 mRNA is expressed in the upper layer of psoriatic epidermis. Also, little expression was detected in normal skin tissues. Therefore, there was confirmed increase in expression of GS21015 mRNA in psoriatic skin tissues as compared to normal skin tissues.

EXAMPLE 7

Expression Analysis of GS21015 by Northern Blotting Method

Expression of GS21015 mRNA in various human tissues was analyzed by carrying out Northern blotting using commercially available membranes into which mRNAs from various human tissues [trade name: GeneHunter (code numbers: MRB-111, MRB-112, MRB-113, MRB-114, MRB-311, and MRB-312), manufactured by Toyobo Co., Ltd.] were blotted.

The hybridization was carried out under the conditions of incubation at 65° C. for 16 hours in a hybridization solution [composition: 6×SSC, 0.5% SDS, 5×Denhardt's solution, 100 μg/ml salmon sperm DNA]. The washing was carried out once at 65° C. for 5 minutes in a washing buffer [composition: 2×SSC, 0.5% SDS], and thereafter twice at 65° C. for 30 minutes in a washing buffer [composition: 0.1×SSC, 0.5% SDS].

As the probe in Northern blotting, there was used a fragment (nucleotide sequence of the cDNA fragment corresponding to 99th to 770th nucleotide sequence of the nucleotide sequence shown in SEQ ID NO: 8) of the GS21015 gene (full length cDNA) obtained in Example 3 mentioned above by labeling with $^{32}P$.

As a result of Northern blotting, strong expression of GS21015 mRNA was found in fetal skin tissues and adult uterus cervical tissues, and weak expression was found in adult uterus tissues and adult prostate tissues. However, expression was not found in other tissues (each of the tissues of brain, heart, lung, liver, small intestine, kidney, and muscle of a fetus, as well as brain, heart, lung, liver, pancreas, spleen, stomach, jejunum, ileum, colon, rectum, kidney, bladder, prostate, testis, ovary, placenta, and muscle of an adult). It has been known that $cPLA_2\alpha$, $cPLA_2\beta$, and $cPLA_2\gamma$ are expressed in almost all the tissues (Pickard et al., *The Journal of Biological Chemistry*, 274, 8823-8831, 1999). In this respect, it was found that the GS21015, of which expression is very specific, is significantly different from the known $cPLA_2$.

EXAMPLE 8

Expression Analysis of GS21015 by Immunostaining Method

Expression of the GS21015 polypeptide in a human skin tissue was analyzed by preparing a polyclonal antibody of GS21015, and carrying out immunostaining of psoriatic skin tissues and normal skin tissues from human using this antibody.

(1) Preparation of Antibody of GS 21015

In order to obtain an antigenic peptide for preparing a polyclonal antibody, a fragment (nucleotide sequence of the fragment corresponding to a nucleotide sequence of 101st to 672nd of the nucleotide sequence shown in SEQ ID NO: 8) of the GS21015 gene (full length cDNA) obtained in Example 3 mentioned above was obtained by carrying out PCR using primers with a restriction enzyme recognition sequence added thereto (a primer having the nucleotide sequence shown in SEQ ID NO: 10 and a primer having the nucleotide sequence shown in SEQ ID NO: 11). The resulting cDNA fragment was subcloned into pGEM-T easy vector (manufactured by Promega). The resulting vector was digested with restriction enzymes EcoRI and NotI, and thereafter the resulting product was subcloned into pGEX-5X-3 vector (manufactured by Invitrogen) digested with the same restriction enzymes. This vector was transfected into *Escherichia coli* JM109 strain, to express the desired peptide (amino acid sequence of the peptide corresponding to 1st to 224th amino acid sequence of the amino acid sequence shown in SEQ ID NO: 9) as a fusion protein added with an amino acid sequence of glutathione-S-transferase on N-terminal thereof. The desired peptide was separated and purified from the supernatant of the lysate of this *Escherichia coli* using Glutathione Sepharose 4B column (manufactured by Amersham).

A mixture obtained by mixing 1 mg of this antigenic peptide and complete Freund's adjuvant (manufactured by Difco) in an equivolume was inoculated to a rabbit by intracutaneous injection to the back and the intramuscular injection in the thigh. After the first inoculation, a mixture of 1 mg of the antigen peptide and complete Freund's adjuvant in an equivolume was inoculated to a rabbit every 2 weeks in the same manner as that of the first inoculation. After one week from the termination of a total of five times of the inoculations, the blood of the rabbit was collected, to prepare immune serum.

(2) Expression Analysis Using Antibody

Immunostaining of tissue sections of psoriatic skin and normal skin from human was carried out using the immune serum prepared in the above (1). The tissue sections of the psoriatic skin and the normal skin were prepared in the same manner as in Example 6 mentioned above. The immunostaining was carried out in accordance with the protocol of ABC-PO (rabbit IGG) kit (manufactured by Vectastein).

As a result, expression of the GS21015 polypeptide was found in the upper layer of psoriatic epidermis as in the results for the analysis of expression of GS21015 mRNA by in situ hybridization method carried out in Example 6 mentioned above, and expression was hardly detected in normal skin tissues. Therefore, there was confirmed increase in expression of the GS21015 polypeptide in psoriatic skin tissues as compared to normal skin tissues.

In other words, it was found that the examination of a psoriatic patient can be performed using expression of a GS21015 gene or polypeptide as an index, and the psoriatic tissues can be detected.

Sequence Free Text

SEQ ID NO: 1 shows an artificially synthesized primer sequence.
SEQ ID NO: 2 shows an artificially synthesized primer sequence.
SEQ ID NO: 3 shows an artificially synthesized primer sequence.
SEQ ID NO: 5 shows an artificially synthesized primer sequence.
SEQ ID NO: 6 shows an artificially synthesized primer sequence.
SEQ ID NO: 7 shows an artificially synthesized primer sequence.
SEQ ID NO: 10 shows an artificially synthesized primer sequence.
SEQ ID NO: 11 shows an artificially synthesized primer sequence.

INDUSTRIAL APPLICABILITY

According to the polypeptide and the nucleic acid of the present invention, there can be enabled studies and development of a therapeutic agent for a disease, especially a therapeutic agent for an inflammatory disease, more specifically, a therapeutic agent for an inflammatory skin disease such as psoriasis, and studies on onset mechanism of an inflammatory disease. In addition, according to the nucleic acid of the present invention, expression or the presence of the polypeptide or the nucleic acid itself of the present invention in a biological sample can be detected, so that the expression can be altered. Moreover, according to the method of characterizing, identifying or screening the phospholipase $A_2$ inhibitor of the present invention, a medicament having high selectivity for the phospholipase $A_2$ of the present invention, concretely, a therapeutic agent for an inflammatory disease, especially a therapeutic agent for an inflammatory skin disease, inter alia, a therapeutic agent for psoriasis can be characterized, identified or screened. The compound capable of selectively inhibiting the phospholipase $A_2$ of the present invention is expected to have excellent therapeutic effects for an inflammatory skin disease (especially chronic intractable skin diseases such as psoriasis). Furthermore, according to the method for examining psoriasis of the present invention, the examination of psoriasis and the detection of the psoriatic tissues can be enabled simply, rapidly and in an excellent sensitivity.

The invention claimed is:

1. A method for identifying or screening a candidate agent for psoriasis, comprising contacting a polypeptide having phospholipase $A_2$ activity with a test substance, assaying an inhibitory action of the test substance on the phospholipase $A_2$ activity of the polypeptide, and determining inhibition on the phospholipase $A_2$ activity, wherein the polypeptide is an isolated and purified polypeptide selected from (a) or (b):
   (a) a polypeptide having the amino acid sequence shown in SEQ ID NO:9; or
   (b) a polypeptide encoded by a nucleic acid capable of hybridizing under high-stringency conditions with the full complement of a nucleic acid having the nucleotide sequence shown in SEQ ID NO:8, wherein hybridization under high-stringency conditions with the full complement is carried out by hybridizing at 65° C. for 16 hours in a hybridization solution (6×SSC, 0.5%SDS, 5× Denhardt's solution, 100 μg/ml salmon sperm DNA), washing at 65° C. for 5 minutes in a washing solution (2×SSC, 0.5%SDS), and thereafter washing twice at 65° C. for 30 minutes in washing solution (0.1×SSC, 0.5%SDS).

2. The method according to claim 1, wherein the action of the test substance is assayed by carrying out an enzymatic reaction in a reaction system comprising the polypeptide having phospholipase $A_2$ activity, a substrate for the phospholipase $A_2$, and the test substance, and assaying an inhibitory action on the enzymatic activity of the phospholipase $A_2$.

3. The method according to claim 2, wherein the substrate is a glycerophospholipid, and the enzymatic activity is an activity for hydrolyzing an ester bond at 2-position of the glycerophospholipid.

4. A diagnostic method for psoriasis, which comprises assaying an expression level of a gene in a biological sample collected from a human, wherein said gene encodes a polypeptide having phospholipase $A_2$ activity selected from (a) or (b):
   (a) a polypeptide having the amino acid sequence shown in SEQ ID NO:9; or
   (b) a polypeptide encoded by a nucleic acid capable of hybridizing under high-stringency conditions with the full complement of a nucleic acid having the nucleotide sequence shown in SEQ ID NO:8, wherein hybridization under high-stringency conditions with the full complement is carried out by hybridizing at 65° C. for 16 hours in a hybridization solution (6×SSC, 0.5%SDS, 5× Denhardt's solution, 100 μg/ml salmon sperm DNA), washing at 65° C. for 5 minutes in a washing solution (2×SSC, 0.5%SDS), and thereafter washing twice at 65° C. for 30 minutes in washing solution (0.1×SSC, 0.5%SDS).

5. The diagnostic method according to claim 4, wherein the expression level is assayed using a probe that is a nucleic acid capable of hybridizing with a nucleic acid having the nucleotide sequence shown in SEQ ID NO:8 under high-stringency conditions or the full complement thereof, wherein hybridization under high-stringency conditions is carried out by hybridizing at 65° C. for 16 hours in a hybridization solution (6×SSC, 0.5% SDS, 5× Denhardt's solution, 100 μg/ml salmon sperm DNA), washing at 65° C. for 5 minutes in a washing solution (6×SSC, 0.5%SDS), and thereafter washing twice at 65° C. for 30 min in washing solution (0.1×SSC).

6. The diagnostic method according to claim 4, wherein the expression level is assayed using a probe or primer comprising the sequence of SEQ ID NO:4 or the full complement thereof.

* * * * *

SEQUENCE LISTING

```
<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 1
gttttcccag tcacgacgtt g                                       21

<210> SEQ ID NO 2
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 2
accatgatta cgccaagctt g                                       21

<210> SEQ ID NO 3
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 3
tgtaaaacga cggccagt                                           18

<210> SEQ ID NO 4
<211> LENGTH: 87
<212> TYPE: DNA
<213> ORGANISM: Homo sapiens

<400> SEQUENCE: 4
gatcatgtgg ttttgtcgtg tattttatta atgtactcta ttgcattaat tggtttttgg    60
```

-continued

```
atattaaacc aactttgcat tcctaaa                                           87

<210> SEQ ID NO 5
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 5
gtacacgaca aaaccacatg a                                                 21

<210> SEQ ID NO 6
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 6
gtccagcgca gccccgcaga gctcc                                             25

<210> SEQ ID NO 7
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 7
aaatacacga caaaaccaca tgatc                                             25

<210> SEQ ID NO 8
<211> LENGTH: 3587
<212> TYPE: DNA
<213> ORGANISM: Homo sapiens
<220> FEATURE:
<221> NAME/KEY: CDS
<222> LOCATION: (99)..(2552)

<400> SEQUENCE: 8
ggccgctgtc ctatcccact gggaccgtcg ctgccactca gccagagagc cagcatcttg       60
gcaagggctg ggcctggagt gaagctggaa gggctagc atg gag agc ctg tca cct      116
                                         Met Glu Ser Leu Ser Pro
                                           1               5 ggg gga cca act ggc cac cct tac cag ggg gag gcc tct acc tgc tgg        164
Gly Gly Pro Thr Gly His Pro Tyr Gln Gly Glu Ala Ser Thr Cys Trp
        10                  15                  20 cag ctc aca gtg agg gtc ctg gag gcg cgg aac ctg cgc tgg gct gac        212
Gln Leu Thr Val Arg Val Leu Glu Ala Arg Asn Leu Arg Trp Ala Asp
    25                  30                  35 ctg ttg agt gag gcc gac cct tac gtg atc cta cag ctg tcg acc gca        260
Leu Leu Ser Glu Ala Asp Pro Tyr Val Ile Leu Gln Leu Ser Thr Ala
40                  45                  50 cct gga atg aag ttt aag acc aag acg ctc acc gac acc agt cat cct        308
Pro Gly Met Lys Phe Lys Thr Lys Thr Leu Thr Asp Thr Ser His Pro
 55                  60                  65                  70 gtg tgg aat gag gcc ttc cgt ttc ctt atc caa agt cag gtc aag aat        356
Val Trp Asn Glu Ala Phe Arg Phe Leu Ile Gln Ser Gln Val Lys Asn
                 75                  80                  85 gtt ctg gag ctt agc atc tat gat gag gac tca gtc acg gag gat gac        404
Val Leu Glu Leu Ser Ile Tyr Asp Glu Asp Ser Val Thr Glu Asp Asp
             90                  95                 100
```

```
atc tgc ttc aag gtt ctc tat gac atc tca gaa gtc ctc cct ggc aag    452
Ile Cys Phe Lys Val Leu Tyr Asp Ile Ser Glu Val Leu Pro Gly Lys
            105                 110                 115 ctg ctc cgg aaa acc ttc tcc cag agt ccc cag gga gag gag gag ctg    500
Leu Leu Arg Lys Thr Phe Ser Gln Ser Pro Gln Gly Glu Glu Glu Leu
    120                 125                 130 gat gtg gag ttc ctg atg gaa gaa acg tca gat cgc cca gaa aac ctc    548
Asp Val Glu Phe Leu Met Glu Glu Thr Ser Asp Arg Pro Glu Asn Leu
135                 140                 145                 150 atc acc aac aaa gtc att gtg gcc cga gag ctg tca tgc ctg gat gtg    596
Ile Thr Asn Lys Val Ile Val Ala Arg Glu Leu Ser Cys Leu Asp Val
                155                 160                 165 cat ctg gac agc aca ggg agc acc gct gtg gtt gca gat cag gac aag    644
His Leu Asp Ser Thr Gly Ser Thr Ala Val Val Ala Asp Gln Asp Lys
            170                 175                 180 ctg gag ctg gag ctg gtg ctg aag ggg tcc tat gag gac aca cag aca    692
Leu Glu Leu Glu Leu Val Leu Lys Gly Ser Tyr Glu Asp Thr Gln Thr
    185                 190                 195 tcc ttc ctg ggc aca gcc tct gcc ttc cgc ttc cac tac atg gca gcc    740
Ser Phe Leu Gly Thr Ala Ser Ala Phe Arg Phe His Tyr Met Ala Ala
200                 205                 210 cta gag aca gag ctg agc ggg cgc ctg agg agc tcc aga agc aat ggc    788
Leu Glu Thr Glu Leu Ser Gly Arg Leu Arg Ser Ser Arg Ser Asn Gly
215                 220                 225                 230 tgg aat ggg gac aac tca gct ggg tac ctc act gtg ccc ctg agg ccc    836
Trp Asn Gly Asp Asn Ser Ala Gly Tyr Leu Thr Val Pro Leu Arg Pro
                235                 240                 245 ttg acc att ggg aag gag gtg act atg gat gtt cct gct cca aat gcc    884
Leu Thr Ile Gly Lys Glu Val Thr Met Asp Val Pro Ala Pro Asn Ala
            250                 255                 260 cca gga gtg agg ctg cag ctc aag gca gag ggc tgc cct gag gag ctg    932
Pro Gly Val Arg Leu Gln Leu Lys Ala Glu Gly Cys Pro Glu Glu Leu
    265                 270                 275 gcc gtg cac ctg ggc ttc aat ctc tgt gca gag gag cag gcc ttc ctg    980
Ala Val His Leu Gly Phe Asn Leu Cys Ala Glu Glu Gln Ala Phe Leu
280                 285                 290 agc agg agg aag cag gtg gtg gcc aag gcc ctg aag cag gcc ctg cag   1028
Ser Arg Arg Lys Gln Val Val Ala Lys Ala Leu Lys Gln Ala Leu Gln
295                 300                 305                 310 ctg gac aga gac ctg cag gag gat gag gta ccc gtt gtg ggc atc atg   1076
Leu Asp Arg Asp Leu Gln Glu Asp Glu Val Pro Val Val Gly Ile Met
            315                 320                 325 gcc aca gga gga ggt gcc cgg gcc atg acc tca ctc tac ggc cac cta   1124
Ala Thr Gly Gly Gly Ala Arg Ala Met Thr Ser Leu Tyr Gly His Leu
    330                 335                 340 ttg gcc ttg cag aag ctg ggc ctc cta gac tgt gtg acc tac ttc agt   1172
Leu Ala Leu Gln Lys Leu Gly Leu Leu Asp Cys Val Thr Tyr Phe Ser
345                 350                 355 ggc atc tct ggc tct acg tgg aca atg gcc cac ctg tac ggg gac cct   1220
Gly Ile Ser Gly Ser Thr Trp Thr Met Ala His Leu Tyr Gly Asp Pro
360                 365                 370 gag tgg tcg cag agg gac ctg gag gga cct atc aga tac gcc cgg gag   1268
Glu Trp Ser Gln Arg Asp Leu Glu Gly Pro Ile Arg Tyr Ala Arg Glu
375                 380                 385                 390 cac ctg gcc aag agc aag ctg gag gtc ttt tcc cca gag cgc ctg gcg   1316
His Leu Ala Lys Ser Lys Leu Glu Val Phe Ser Pro Glu Arg Leu Ala
            395                 400                 405 agc tac cgc cgg gag ctg gag ctg cgg gct gag cag ggc cac ccc acg   1364
Ser Tyr Arg Arg Glu Leu Glu Leu Arg Ala Glu Gln Gly His Pro Thr
```

-continued

```
              410                 415                 420
acc ttt gtg gac ctg tgg gcg cta gtg ctg gag tcc atg ctg cac ggc    1412
Thr Phe Val Asp Leu Trp Ala Leu Val Leu Glu Ser Met Leu His Gly
        425                 430                 435 cag gtg atg gat cag aag ctg tca gga cag aga gcc gcc ctg gaa cgg    1460
Gln Val Met Asp Gln Lys Leu Ser Gly Gln Arg Ala Ala Leu Glu Arg
        440                 445                 450 ggt cag aac cct ctg ccc ctc tac ttg agc ctc aat gtc aaa gag aac    1508
Gly Gln Asn Pro Leu Pro Leu Tyr Leu Ser Leu Asn Val Lys Glu Asn
455                 460                 465                 470 aat ctg gag aca ctg gac ttc aag gag tgg gtt gag ttc tcc ccc tat    1556
Asn Leu Glu Thr Leu Asp Phe Lys Glu Trp Val Glu Phe Ser Pro Tyr
                475                 480                 485 gag gtc ggt ttc ctg aag tac ggg gcc ttc gtc cct cct gag ctc ttc    1604
Glu Val Gly Phe Leu Lys Tyr Gly Ala Phe Val Pro Pro Glu Leu Phe
            490                 495                 500 ggc tcc gag ttc ttc atg gga cgg ctg atg agg agg atc ccg gag ccc    1652
Gly Ser Glu Phe Phe Met Gly Arg Leu Met Arg Arg Ile Pro Glu Pro
        505                 510                 515 cgg atc tgc ttt ctg gaa gcc atc tgg agc aac att ttc tcc ctg aac    1700
Arg Ile Cys Phe Leu Glu Ala Ile Trp Ser Asn Ile Phe Ser Leu Asn
        520                 525                 530 ctg ctg gat gcc tgg tat gac ctc acc agt tct ggg gag tcc tgg aaa    1748
Leu Leu Asp Ala Trp Tyr Asp Leu Thr Ser Ser Gly Glu Ser Trp Lys
535                 540                 545                 550 cag cac atc aag gac aag acc agg agc tta gag aag gag ccc ctg acc    1796
Gln His Ile Lys Asp Lys Thr Arg Ser Leu Glu Lys Glu Pro Leu Thr
                555                 560                 565 acc tcg ggg acc tcc tcg cgg ctg gag gcc tcg tgg ctg cag cca ggc    1844
Thr Ser Gly Thr Ser Ser Arg Leu Glu Ala Ser Trp Leu Gln Pro Gly
            570                 575                 580 acg gcg ctg gcc cag gca ttt aaa ggc ttc ctg aca ggc agg ccc ctc    1892
Thr Ala Leu Ala Gln Ala Phe Lys Gly Phe Leu Thr Gly Arg Pro Leu
        585                 590                 595 cac cag cgc agc ccc aac ttc ctc cag ggc ctc cag ctg cac cag gac    1940
His Gln Arg Ser Pro Asn Phe Leu Gln Gly Leu Gln Leu His Gln Asp
        600                 605                 610 tac tgt agc cac aaa gac ttc tcc acc tgg gca gac tac cag ctt gac    1988
Tyr Cys Ser His Lys Asp Phe Ser Thr Trp Ala Asp Tyr Gln Leu Asp
615                 620                 625                 630 tcc atg ccc agc cag ctg acc ccc aag gag ccc cgg ctc tgc ctg gtg    2036
Ser Met Pro Ser Gln Leu Thr Pro Lys Glu Pro Arg Leu Cys Leu Val
                635                 640                 645 gac gcc gcc tac ttc atc aac acc agc tct ccc tcc atg ttc cgg cca    2084
Asp Ala Ala Tyr Phe Ile Asn Thr Ser Ser Pro Ser Met Phe Arg Pro
            650                 655                 660 ggc cgc agg ctg gac ctc atc ctc tcc ttc gac tac tcc cta tct gcg    2132
Gly Arg Arg Leu Asp Leu Ile Leu Ser Phe Asp Tyr Ser Leu Ser Ala
        665                 670                 675 ccc ttc gag gca ctg cag cag acg gag ctg tac tgc cgg gcc cgg ggg    2180
Pro Phe Glu Ala Leu Gln Gln Thr Glu Leu Tyr Cys Arg Ala Arg Gly
        680                 685                 690 ctg ccc ttc ccc cgg gtg gaa ccc agc cct cag gac cag cac cag cca    2228
Leu Pro Phe Pro Arg Val Glu Pro Ser Pro Gln Asp Gln His Gln Pro
695                 700                 705                 710 agg gaa tgc cac ctc ttc tca gac ccc gcc tgc ccc gag gcc ccg atc    2276
Arg Glu Cys His Leu Phe Ser Asp Pro Ala Cys Pro Glu Ala Pro Ile
                715                 720                 725 ctg ctg cac ttc ccg ctg gtc aat gcc tcc ttc aag gac cac tca gcc    2324
```

```
Leu Leu His Phe Pro Leu Val Asn Ala Ser Phe Lys Asp His Ser Ala
            730                 735                 740 ccc ggt gtc cag cgc agc ccc gca gag ctc cag ggt ggc caa gtg gat      2372
Pro Gly Val Gln Arg Ser Pro Ala Glu Leu Gln Gly Gly Gln Val Asp
        745                 750                 755 ctc acc ggg gcc acc tgc ccc tac acc ctg tcc aac atg acc tac aag      2420
Leu Thr Gly Ala Thr Cys Pro Tyr Thr Leu Ser Asn Met Thr Tyr Lys
760                 765                 770 gag gaa gac ttc gag cgc ctg ctg cgg ctc agt gac tac aac gtg cag      2468
Glu Glu Asp Phe Glu Arg Leu Leu Arg Leu Ser Asp Tyr Asn Val Gln
775                 780                 785                 790 acc agc cag ggt gcc atc ctg cag gcc ctg agg acc gcg ctg aag cac      2516
Thr Ser Gln Gly Ala Ile Leu Gln Ala Leu Arg Thr Ala Leu Lys His
            795                 800                 805 cgg act cta gag gcg agg cct cca agg gca cag acc tgaggttgct           2562
Arg Thr Leu Glu Ala Arg Pro Pro Arg Ala Gln Thr
            810                 815 cagaggctgc aggaccctcc agggcctgcg ggcataacct gatctgtagc tgggctcagc    2622
cacaggcctt cctggttgga gttctgggct ctcccaggcc tgggtggcct ctgtagctgg    2682
tctcactgcc cagagggaac tgcacacaca gacttctctc ttacgttcat ggctggcttg    2742
agatgagttg aaaataactt cgccaggcca gtgtgtagaa cagctggtcc aaccagacag    2802
actttcacac acaattact tccatgcctg agcaggatag atttgaagtg caagccggag     2862
gcagcagatc aggagtaggg acaggaagga caggggatgc ctgacctgac aggtggcttc    2922
aggcctcggg aatcacaaga catcctgaac acattgcctc ctcatcttct tcctgctcct    2982
ccacctcctc ctctccttgt ccttctcctc tttgtcctcc tgctttccgt atccaagtct    3042
tgtacttgtt taaatttatt cctaaatatt ttattctttt tgataagtgg agttactttc    3102
ttaatttcat ttagattatt cattgctatt ttatagaaat acaatggatt tttaaatgtt    3162
gatcttgtat tccgcaatct tgctgaagtt gtttaccggc tctaatactt ttgcggattt    3222
cttagaattt tctgtagaca gatcatgcca tctccaaata gagatggttt tacttcttcc    3282
tgtctgatct gaatgccttt tatttatttt tcccaattgc cctgagcagt acaatgatga    3342
acacacgttt caagagcaga catcttgtct tgttcctgac tctgacaaga aagcataagt    3402
ctctcaccat ttagtgtgat tttagctgtg ggttttcttt ggacatcctt atcaggttga    3462
gaaagttctc tttatttct agtttattga gtgttttatg atgaaacggt gttaggtttt     3522
gtcaagtgat ttttctgtgt ctatgggcat gatcatgtgg ttttgtcgtg tattttatta    3582
atgta                                                               3587

<210> SEQ ID NO 9
<211> LENGTH: 818
<212> TYPE: PRT
<213> ORGANISM: Homo sapiens

<400> SEQUENCE: 9

Met Glu Ser Leu Ser Pro Gly Gly Pro Thr Gly His Pro Tyr Gln Gly
1               5                   10                  15

Glu Ala Ser Thr Cys Trp Gln Leu Thr Val Arg Val Leu Glu Ala Arg
            20                  25                  30

Asn Leu Arg Trp Ala Asp Leu Leu Ser Glu Ala Asp Pro Tyr Val Ile
        35                  40                  45

Leu Gln Leu Ser Thr Ala Pro Gly Met Lys Phe Lys Thr Lys Thr Leu
    50                  55                  60
```

-continued

```
Thr Asp Thr Ser His Pro Val Trp Asn Glu Ala Phe Arg Phe Leu Ile
 65                  70                  75                  80

Gln Ser Gln Val Lys Asn Val Leu Glu Leu Ser Ile Tyr Asp Glu Asp
             85                  90                  95

Ser Val Thr Glu Asp Asp Ile Cys Phe Lys Val Leu Tyr Asp Ile Ser
            100                 105                 110

Glu Val Leu Pro Gly Lys Leu Leu Arg Lys Thr Phe Ser Gln Ser Pro
            115                 120                 125

Gln Gly Glu Glu Glu Leu Asp Val Glu Phe Leu Met Glu Glu Thr Ser
130                 135                 140

Asp Arg Pro Glu Asn Leu Ile Thr Asn Lys Val Ile Val Ala Arg Glu
145                 150                 155                 160

Leu Ser Cys Leu Asp Val His Leu Asp Ser Thr Gly Ser Thr Ala Val
                165                 170                 175

Val Ala Asp Gln Asp Lys Leu Glu Leu Glu Leu Val Leu Lys Gly Ser
            180                 185                 190

Tyr Glu Asp Thr Gln Thr Ser Phe Leu Gly Thr Ala Ser Ala Phe Arg
            195                 200                 205

Phe His Tyr Met Ala Ala Leu Glu Thr Glu Leu Ser Gly Arg Leu Arg
210                 215                 220

Ser Ser Arg Ser Asn Gly Trp Asn Gly Asp Asn Ser Ala Gly Tyr Leu
225                 230                 235                 240

Thr Val Pro Leu Arg Pro Leu Thr Ile Gly Lys Glu Val Thr Met Asp
                245                 250                 255

Val Pro Ala Pro Asn Ala Pro Gly Val Arg Leu Gln Leu Lys Ala Glu
            260                 265                 270

Gly Cys Pro Glu Glu Leu Ala Val His Leu Gly Phe Asn Leu Cys Ala
            275                 280                 285

Glu Glu Gln Ala Phe Leu Ser Arg Arg Lys Gln Val Val Ala Lys Ala
            290                 295                 300

Leu Lys Gln Ala Leu Gln Leu Asp Arg Asp Leu Gln Glu Asp Glu Val
305                 310                 315                 320

Pro Val Val Gly Ile Met Ala Thr Gly Gly Ala Arg Ala Met Thr
                325                 330                 335

Ser Leu Tyr Gly His Leu Leu Ala Leu Gln Lys Leu Gly Leu Leu Asp
            340                 345                 350

Cys Val Thr Tyr Phe Ser Gly Ile Ser Gly Ser Thr Trp Thr Met Ala
            355                 360                 365

His Leu Tyr Gly Asp Pro Glu Trp Ser Gln Arg Asp Leu Glu Gly Pro
370                 375                 380

Ile Arg Tyr Ala Arg Glu His Leu Ala Lys Ser Lys Leu Glu Val Phe
385                 390                 395                 400

Ser Pro Glu Arg Leu Ala Ser Tyr Arg Arg Glu Leu Glu Leu Arg Ala
                405                 410                 415

Glu Gln Gly His Pro Thr Thr Phe Val Asp Leu Trp Ala Leu Val Leu
            420                 425                 430

Glu Ser Met Leu His Gly Gln Val Met Asp Gln Lys Leu Ser Gly Gln
            435                 440                 445

Arg Ala Ala Leu Glu Arg Gly Gln Asn Pro Leu Pro Leu Tyr Leu Ser
450                 455                 460

Leu Asn Val Lys Glu Asn Asn Leu Glu Thr Leu Asp Phe Lys Glu Trp
465                 470                 475                 480

Val Glu Phe Ser Pro Tyr Glu Val Gly Phe Leu Lys Tyr Gly Ala Phe
```

```
                485                 490                 495
Val Pro Pro Glu Leu Phe Gly Ser Glu Phe Met Gly Arg Leu Met
            500                 505                 510

Arg Arg Ile Pro Glu Pro Arg Ile Cys Phe Leu Glu Ala Ile Trp Ser
        515                 520                 525

Asn Ile Phe Ser Leu Asn Leu Leu Asp Ala Trp Tyr Asp Leu Thr Ser
        530                 535                 540

Ser Gly Glu Ser Trp Lys Gln His Ile Lys Asp Lys Thr Arg Ser Leu
545                 550                 555                 560

Glu Lys Glu Pro Leu Thr Thr Ser Gly Thr Ser Arg Leu Glu Ala
                565                 570                 575

Ser Trp Leu Gln Pro Gly Thr Ala Leu Ala Gln Ala Phe Lys Gly Phe
            580                 585                 590

Leu Thr Gly Arg Pro Leu His Gln Arg Ser Pro Asn Phe Leu Gln Gly
            595                 600                 605

Leu Gln Leu His Gln Asp Tyr Cys Ser His Lys Asp Phe Ser Thr Trp
610                 615                 620

Ala Asp Tyr Gln Leu Asp Ser Met Pro Ser Gln Leu Thr Pro Lys Glu
625                 630                 635                 640

Pro Arg Leu Cys Leu Val Asp Ala Ala Tyr Phe Ile Asn Thr Ser Ser
            645                 650                 655

Pro Ser Met Phe Arg Pro Gly Arg Arg Leu Asp Leu Ile Leu Ser Phe
            660                 665                 670

Asp Tyr Ser Leu Ser Ala Pro Phe Glu Ala Leu Gln Gln Thr Glu Leu
            675                 680                 685

Tyr Cys Arg Ala Arg Gly Leu Pro Phe Pro Arg Val Glu Pro Ser Pro
690                 695                 700

Gln Asp Gln His Gln Pro Arg Glu Cys His Leu Phe Ser Asp Pro Ala
705                 710                 715                 720

Cys Pro Glu Ala Pro Ile Leu Leu His Phe Pro Leu Val Asn Ala Ser
                725                 730                 735

Phe Lys Asp His Ser Ala Pro Gly Val Gln Arg Ser Pro Ala Glu Leu
            740                 745                 750

Gln Gly Gly Gln Val Asp Leu Thr Gly Ala Thr Cys Pro Tyr Thr Leu
            755                 760                 765

Ser Asn Met Thr Tyr Lys Glu Glu Asp Phe Glu Arg Leu Leu Arg Leu
            770                 775                 780

Ser Asp Tyr Asn Val Gln Thr Ser Gln Gly Ala Ile Leu Gln Ala Leu
785                 790                 795                 800

Arg Thr Ala Leu Lys His Arg Thr Leu Glu Ala Arg Pro Pro Arg Ala
                805                 810                 815

Gln Thr
```

<210> SEQ ID NO 10
<211> LENGTH: 31
<212> TYPE: DNA
<213> ORGANISM: Artificial Sequence
<220> FEATURE:
<223> OTHER INFORMATION: Artificially synthesized primer sequence

<400> SEQUENCE: 10
gatcgaattc catggagagc ctgtcacctg g          31

<210> SEQ ID NO 11
<211> LENGTH: 30

```
<212> TYPE: DNA
<213> ORGANISM: Artificial Sequence
<220> FEATURE:
<223> OTHER INFORMATION: Artificially synthesized primer sequence

<400> SEQUENCE: 11
gatcgcggcc gctgcccaag cctaggattg                                         30
```